United States Patent [19]

Maraganore et al.

[11] Patent Number: 5,182,260
[45] Date of Patent: Jan. 26, 1993

[54] DNA SEQUENCES ENCODING SNAKE VENOM INHIBITORS OF PLATELET ACTIVATION PROCESSES FOR PRODUCING THOSE INHIBITORS AND COMPOSITIONS USING THEM

[75] Inventors: John M. Maraganore, Tewksbury, Mass.; Joseph A. Jakubowski, Indianapolis, Ind.

[73] Assignees: Biogen, Inc., Cambridge; Trustees of Boston University, Boston, both of Mass.

[21] Appl. No.: 430,313

[22] Filed: Nov. 1, 1989

Related U.S. Application Data

[63] Continuation-in-part of Ser. No. 303,585, Jan. 27, 1989, abandoned, and a continuation-in-part of Ser. No. 303,590, Jan. 27, 1989, abandoned.

[51] Int. Cl.$^5$ .................. A61K 37/00; C07K 13/00; C12N 15/12
[52] U.S. Cl. ............................ 514/12; 530/324; 530/856; 530/350; 435/69.1; 435/69.6; 435/320.1; 435/240.1; 536/23.5
[58] Field of Search ............... 530/324, 350, 856; 514/12; 435/69.1, 69.6, 320, 240.1; 536/27

[56] References Cited

U.S. PATENT DOCUMENTS

| | | | |
|---|---|---|---|
| 3,743,722 | 7/1973 | Nolan | 424/98 |
| 3,879,369 | 4/1975 | Nolan | 260/112 R |
| 4,341,762 | 7/1982 | Haast | 424/88 |
| 4,578,079 | 3/1986 | Ruoslahti et al. | 623/11 |
| 4,683,291 | 7/1987 | Zimmerman et al. | 530/324 |
| 4,741,902 | 5/1988 | Haast | 424/88 |

FOREIGN PATENT DOCUMENTS 0317053 5/1989 European Pat. Off.
0338634 10/1989 European Pat. Off.

OTHER PUBLICATIONS

Huany et al., "Trigramin" J. Biol. Chem. v262(33) Nov. 25, 1987, pp. 16157–16163.
Huang et al., "Characterization of a Potent Platelet Aggregation Inhibitor . . . ", Bioch. Biophys Acta 925, pp. 248–257 (1987).
Huang et al., "Trigramin: Primary Structure . . . ", Biochemistry 28, pp. 661–666, Jan. 24, 1989.
Dennis et al., "Platelet Glycoprotein II6–III9 Protein Antagonists from Snake Venom . . . ", Proc. Natl. Acad. Sci. USA, 87, pp. 2471–2475, 1990.
Bajwa et al. "Thrombin-Like and Fibrinolytic Enzymes in the Venoms from the Gaboon Viper . . . ", toxicon, 20,, pp. 427–432 (1982).
Chao et al., "Agkistrodon Piscivorus Piscivorus Platelet Aggregation Inhibitor . . . ", Proc. Natl. Acad. Sci. USA, 86, pp. 8050–8054, (Oct. 1989).
Gan et al., "A Potent Platelet Aggregation Inhibitor . . . ", The Journal of Biological Chemistry, 968, pp. 19827–19832 (1988).

(List continued on next page.)

Primary Examiner—Garnette D. Draper
Assistant Examiner—Nina Ossanna
Attorney, Agent, or Firm—Leon R. Yankwich; James F. Haley, Jr.; Andrew S. Marks

[57] ABSTRACT

The present invention relates to polypeptide inhibitors of platelet activation and derivatives thereof, purified from the venom of the North American Water Moccasin and to methods for their purification. This invention also relates to DNA sequences and recombinant DNA molecules which code for these polypeptide inhibitors of platelet activation. And this invention relates to recombinant DNA molecules which code for fusion proteins comprising both a polypeptide inhibitor of platelet activation and an anti-thrombin polypeptide. This invention also relates to pharmaceutically acceptable compositions and methods characterized by at least one of these natural or recombinant inhibitors of platelet activation, alone or in combination with anti-thrombin compounds. The compositions, combinations and methods of this invention are particularly useful in the treatment of thrombotic diseases.

9 Claims, 13 Drawing Sheets

OTHER PUBLICATIONS

Huang et al., "Characterization of Hemorrhagic Principles From Trimeresurus Gramineus Snake Venom", *Toxicon*, 22, pp. 45–52 (1984).

Knudsen, et al., "Trigtamin, an RGD-Containing Peptide from Snake Venom . . . ", *Experimental Cell Research*, 179, pp. 42–49 (1988).

Ouyang et al. "Potent Platelet Aggregation Inhibitor from Trimeresurus Gramineus Snake Venom", *Biochimica et Biophysica Acta*, 757, pp. 332–341 (1983).

Ouyang et al., "Characterization of the Platelet Aggregation Inducer and Inhibitor . . . ", *Biochimica et Biophysica Acta*, 841, pp. 1–7 (1985).

Teng et al., "Properties of a Potent Platelet Aggregation Inhibitor from *Echis carinatus* Snake Venom", in *Hemostasis and Animal Venoms*, H. Pirkle et al., eds., Marcel Dekker Inc., New York, pp. 399–409 (1988).

FIG.9

```
         DNS                B    X                                    E
         sct                s    h                                    a
         aoy                m    o                                    e
         111                1    2                                    1
         //                 \    /                                    \
         CATGGAAGCTGGTGAAGAATGCGACTGCGGATCCCCGGAAAACCCGTGCTGCGACGCGG
1        ---------+---------+---------+---------+---------+---------+ 60
         GGTACCTTCGACCACTTCTTACGCTGACGCCTAGGGGCCTTTTGGGCACGACGCTGCGCC MetGluAlaGlyGluGluCysAspCysGlySerProGluAsnProCysCysAspAlaAla B                A    BM
                 s                p    sg     D
                 p                a    pi     r
                 M                L    1A     a
                 1                1    21     3
                 \                \    /
         CCACCTGCAAACTTCGTCCGGGTGCACAGTGTGCAGAAGGTCTGTGCTGCGACCAGTGCA
61       ---------+---------+---------+---------+---------+---------+120
         GGTGGACGTTTGAAGCAGGCCCACGTGTCACACGTCTTCCAGACACGACGCTGGTCACGT ThrCysLysLeuArgProGlyAlaGlnCysAlaGluGlyLeuCysCysAspGlnCysLys B               A                   BH               H
         s               sB   K              AsgX             iH
         p               pa   p              vpih             np
         E               7n   n              alAo             ca
         1               11   1              1211             21
         \               \    /              \//              /
         AATTCATGAAAGAAGGTACCGTTTGCCGTCGTGCTCGAGGTGACGACGTTAACGACTACT
121      ---------+---------+---------+---------+---------+---------+180
         TTAAGTACTTTCTTCCATGGCAAACGGCAGCACGAGCTCCACTGCTGCAATTGCTGATGA PheMetLysGluGlyThrValCysArgArgAlaArgGlyAspAspValAsnAspTyrCys B                              H
         s             P                i
         p             s                n
         M             t                d
         1             1                3
         GCAACGGTATCTCTGCAGGTTGCCCGCGTAACCCGTTCCACTGATGA
181      ---------+---------+---------+---------+---- 232
         CGTTGCCATAGAGACGTCCAACGGGCGCATTGGGCAAGGTGACTACTTCGA AsnGlyIleSerAlaGlyCysProArgAsnProPheHisEndEndSer???
```

FIG.10

| | |
|---|---|
| 1 | CATGGAAGCTGGTGAAGAATGCG |
| 2 | CTTCGACCACTTCTTACGCTGACGCCTAGGG |
| | |
| 3 | GATCCCCGGAAAACCCGTGCTGCGACGC |
| 4 | GCCTTTTGGGCACGACGCTGCGCCGGTG |
| | |
| 5 | GGCCACCTGCAAACTTCGTCCGGGTGCACAGTGT |
| 6 | GACGTTTGAAGCAGGCCCACGT |
| | |
| 7 | GCAGAAGGTCTGTGCTGCGACCAGTGCAAAT |
| 8 | GTCACACGTCTTCCAGACACGACGCTGGTCACGTTTAAGTACT |
| | |
| 9 | TCATGAAAGAAGGTACCGTTTGCCGTCGTGC |
| 10 | TTCTTCCATGGCAAACGGCAGCACGAGCTCC |
| | |
| 11 | TCGAGGTGACGACGTTAACGACTACTGCAACGG |
| 12 | ACTGCTGCAATTGCTGATGACGAAGCCATAGAG |
| | |
| 13 | TATCTCTGCAGGTTGCCCGCGTAACCCGTTCCACTGATGA |
| 14 | ACGTCCAACGGGCGCATTGGGCAAGGTGACTACTTCGA |

FIG.11

```
                              H                    E
N     N     S                 i              K  S  c           B
h     o     a                 n              p  m  o           g
e     t     c                 d              n  a  R           l
1     1     2                 3              1  1  1           2
GCTAGCGGCCGCGGTCCAACCACCAATCTCAAAGCTTGGTACCCGGGAATTCAGATCTGC
---------+---------+---------+---------+---------+---------+
CGATCGCCGGCGCCAGGTTGGTGGTTAGAGTTTCGAACCATGGGCCCTTAAGTCTAGACG

E              B
P     SX    SX          c  C     N     a                      NS
s     ph    ab          o  l     c     m                      oa
t     ho    ca          R  a     o     H                      tc
1     11    11          5  1     1     1                      12
              /                                                 /
AGCATGCTCGAGCTCTAGATATCGATTCCATGGATCCTCACATCCCAATCCGCGGCCGCA
---------+---------+---------+---------+---------+---------+
TCGTACGAGCTCGAGATCTATAGCTAAGGTACCTAGGAGTGTAGGGTTAGGCGCCGGCGT
```

FIG.13

```
   1- 50   GAATTCTTAC ACTTAGTTAA ATTGCTAACT TTATAGATTA CAAAACTTAG
  51-100   GAGGGTTTTT ACCATGGGTC CAGAAACCCT GTGCGGCGCT GAGCTGGTGG
 101-150   ACGCTCTGCA GTTTGTGTGC GGTGACCGTG GATTCTACTT CAACAAACCG
 151-200   ACTGGTTACG GATCCTCCTC GAGGCGTGCT CCTCAGACTG GAATCGTCGA
 201-250   CGAATGTTGT TTCCGTTCTT GCGACCTGAG GCGTCTAGAA ATGTACTGCG
 251-300   CGCCGCTGAA ACCGGCGAAG AGTGCATAGA TCCGTCGACC TGCAGCCAAG
 301-350   CTTGGCTGCC TCGCGCGTTT CGGTGATGAC GGTGAAAACC TCTGACACAT
 351-400   GCAGCTCCCG GAGACGGTCA CAGCTTGTCT GTAAGCGGAT GCCGGGAGCA
 401-450   GACAAGCCCG TCAGGGCGCG TCAGCGGGTG TTGGCGGGTG TCGGGGCGCA
 451-500   GCCATGACCC AGTCACGTAG CGATAGCGGA GTGTATACTG GCTTAACTAT
 501-550   GCGGCATCAG AGCAGATTCT ACTGAGAGTG CACCATATGC GGTGTGAAAT
 551-600   ACCGCACAGA TGCGTAAGGA GAAAATACCG CATCAGGCGC TCTTCCGCTT
 601-650   CCTCGCTCAC TGACTCGCTG CGCTCGGTCG TTCGGCTGCG GCGAGCGGTA
 651-700   TCAGCTCACT CAAAGGCGGT AATACGGTTA TCCACAGAAT CAGGGGATAA
 701-750   CGCAGGAAAG AACATGTGAG CAAAAGGCCA GCAAAAGGCC AGGAACCGTA
 751-800   AAAAGGCCGC GTTGCTGGCG TTTTTCCATA GGCTCCGCCC CCCTGACGAG
 801-850   CATCACAAAA ATCGACGCTC AAGTCAGAGG TGGCGAAACC CGACAGGACT
 851-900   ATAAAGATAC CAGGCGTTTC CCCCTGGAAG CTCCCTCGTG CGCTCTCCTG
 901-950   TTCCGACCCT GCCGCTTACC GGATACCTGT CCGCCTTTCT CCCTTCGGGA
 950-000   AGCGTGGCGC TTTCTCAATG CTCACGCTGT AGGTATCTCA GTTCGGTGTA
1001-050   GGTCGTTCGC TCCAAGCTGG GCTGTGTGCA CGAACCCCCC GTTCAGCCCG
1051-100   ACCGCTGCGC CTTATCCGGT AACTATCGTC TTGAGTCCAA CCCGGTAAGA
1101-150   CACGACTTAT CGCCACTGGC AGCAGCCACT GGTAACAGGA TTAGCAGAGC
1151-200   GAGGTATGTA GGCGGTGCTA CAGAGTTCTT GAAGTGGTGG CCTAACTACG
1201-250   GCTACACTAG AAGGACAGTA TTTGGTATCT GCGCTCTGCT GAAGCCAGTT
1251-300   ACCTTCGGAA AAAGAGTTGG TAGCTCTTGA TCCGGCAAAC AAACCACCGC
1301-350   TGGTAGCGGT GGTTTTTTTG TTTGCAAGCA GCAGATTACG CGCAGAAAAA
1351-400   AAGGATCTCA AGAAGATCCT TTGATCTTTT CTACGGGGTC TGACGCTCAG
1401-450   TGGAACGAAA ACTCACGTTA AGGGATTTTG GTCATGAGAT TATCAAAAAG
1451-500   GATCTTCACC TAGATCCTTT TAAATTAAAA ATGAAGTTTT AAATCAATCT
1501-550   AAAGTATATA TGAGTAAACT TGGTCTGACA GTTACCAATG CTTAATCAGT
```

FIG.13 (cont'd)

```
1551-600   GAGGCACCTA TCTCAGCGAT CTGTCTATTT CGTTCATCCA TAGTTGCCTG
1601-650   ACTCCCCGTC GTGTAGATAA CTACGATACG GGAGGGCTTA CCATCTGGCC
1651-700   CCAGTGCTGC AATGATACCG CGAGACCCAC GCTCACCGGC TCCAGATTTA
1701-750   TCAGCAATAA ACCAGCCAGC CGGAAGGGCC GAGCGCAGAA GTGGTCCTGC
1751-800   AACTTTATCC GCCTCCATCC AGTCTATTAA TTGTTGCCGG GAAGCTAGAG
1801-850   TAAGTAGTTC GCCAGTTAAT AGTTTGCGCA ACGTTGTTGC CATTGCTGCA
1851-900   GGCATCGTGG TGTCACGCTC GTCGTTTGGT ATGGCTTCAT TCAGCTCCGG
1901-950   TTCCCAACGA TCAAGGCGAG TTACATGATC CCCCATGTTC TGCAAAAAAG
1951-000   CGGTTAGCTC CTTCGGTCCT CCGATCGTTG TCAGAAGTAA GTTGGCCGCA
2001-050   GTGTTATCAC TCATGGTTAT GGCAGCACTG CATAATTCTC TTACTGTCAT
2051-100   GCCATCCGTA AGATGCTTTT CTGTGACTGG TGAGTACTCA ACCAAGTCAT
2101-150   TCTGAGAATA GTGTATGCGG CGACCGAGTT GCTCTTGCCC GGCGTCAACA
2151-200   CGGGATAATA CCGCGCCACA TAGCAGAACT TTAAAAGTGC TCATCATTGG
2201-250   AAAACGTTCT TCGGGGCGAA AACTCTCAAG GATCTTACCG CTGTTGAGAT
2251-300   CCAGTTCGAT GTAACCCACT CGTGCACCCA ACTGATCTTC AGCATCTTTT
2301-350   ACTTTCACCA GCGTTTCTGG GTGAGCAAAA ACAGGAAGGC AAAATGCCGC
2351-400   AAAAAAGGGA ATAAGGGCGA CACGGAAATG TTGAATACTC ATACTCTTCC
2401-450   TTTTTCAATA TTATTGAAGC AGACAGTTTT ATTGTTCATG ATGATATATT
2451-500   TTTATCTTGT GCAATGTAAC ATCAGAGATT TTGAGACACA ACGTGGCTTT
2501-550   GTTGAATAAA TCGAACTTTT GCTGAGTTGA AGGATCAGAT CACGCATCTT
2551-600   CCCGACAACG CAGACCGTTC CGTGGCAAAG CAAAAGTTCA AAATCACCAA
2601-650   CTGGTCCAAC CTACAACAAA GCTCTCATCA ACCGTGGCTC CCTCACTTTC
2651-700   TGGCTGGATG ATGGGGCGAT TCAGGCCTGG TATGAGTCAG CAACACCTTC
2701-750   TTCACGAGGC AGACCTCAGC GCCGGTGATG CCGGCCACGA TGCGTCCGGC
2751-800   GTAGAGGATC TCTCACCTAC CAAACAATGC CCCCCTGCAA AAAAATAAAT
2801-850   TCATATAAAA AACATACAGA TAACCATCTG CGGTGATAAA TTATCTCTGG
2851-900   CGGTGTTGAC ATAAATACCA CTGGCGGTGA TACTGAGCAC ATCAGCAGGA
2901-950   CGCACTGACC ACCATGAAGG TGACGCTCTT AAAATTAAGC CCTGAAGAAG
2951-000   GGCAGCATTC AAAGCAGAAG GCTTTGGGGT GTGTGATACG AAACGAAGCA
3001-003   TTG
```

FIG. 14
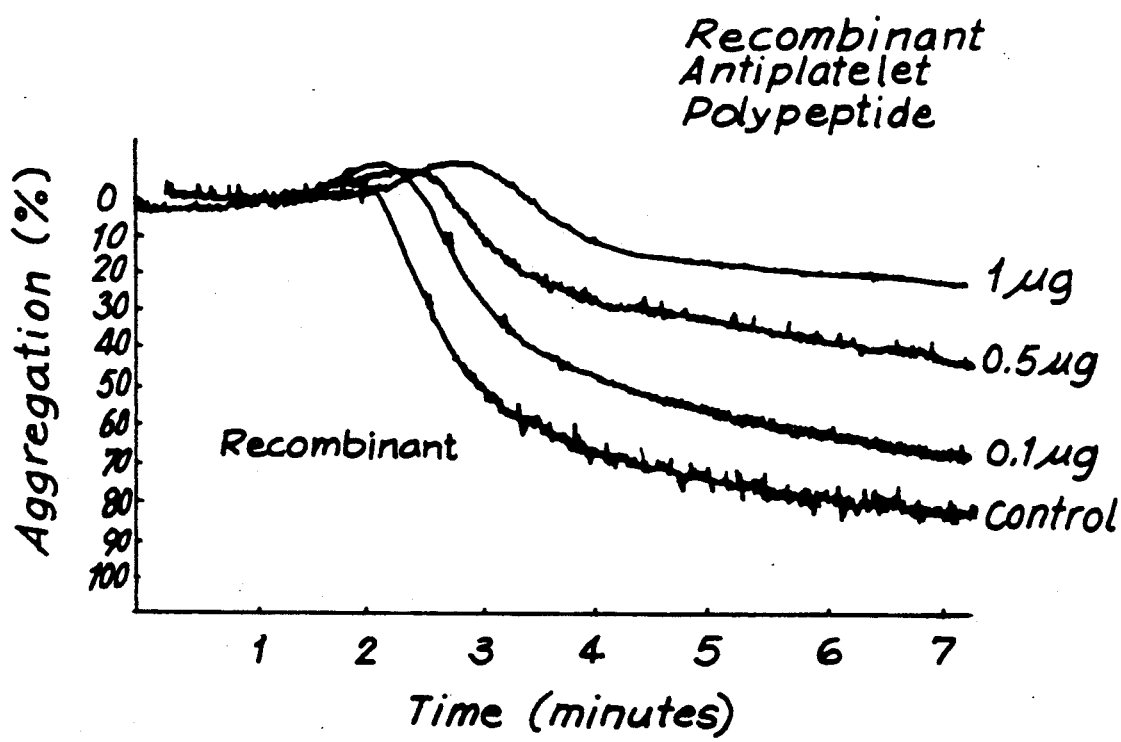
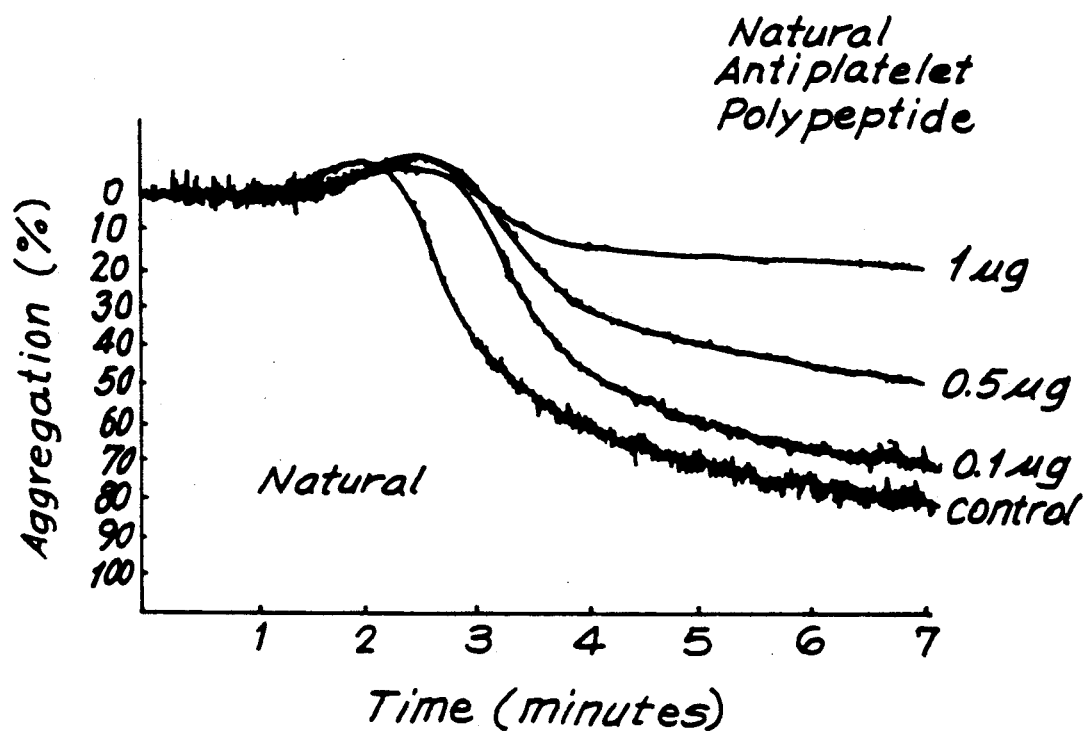

DNA SEQUENCES ENCODING SNAKE VENOM INHIBITORS OF PLATELET ACTIVATION PROCESSES FOR PRODUCING THOSE INHIBITORS AND COMPOSITIONS USING THEM

CROSS-REFERENCE TO RELATED APPLICATIONS

This application is a continuation-in-part of U.S. patent application Ser. No. 303,585, now abandoned and U.S. patent application Ser. No. 303,590, now abandoned both filed on Jan. 27, 1989.

TECHNICAL FIELD OF THE INVENTION

The present invention relates to polypeptide inhibitors of platelet activation and derivatives thereof, purified from the venom of the North American Water Moccasin and to methods for their purification. This invention also relates to DNA sequences and recombinant DNA molecules which code for these polypeptide inhibitors of platelet activation. And this invention relates to recombinant DNA molecules which code for fusion proteins comprising both a polypeptide inhibitor of platelet activation and an anti-thrombin polypeptide. This invention also relates to pharmaceutically acceptable compositions and methods characterized by at least one of these natural or recombinant inhibitors of platelet activation, alone or in combination with anti-thrombin compounds. The compositions, combinations and methods of this invention are particularly useful in the treatment of thrombotic diseases.

BACKGROUND ART

Platelet aggregation and release reactions (collectively known as platelet activation) are essential to hemostasis. However, perturbations in platelet mechanisms controlling hemostasis may yield thrombi (blood clots) which are pathogenic when blood flow to dependent tissues is occluded. This is the case in a variety of life-threatening vascular diseases, such as myocardial infarction, stroke, pulmonary embolism, deep vein thrombosis, peripheral arterial occlusion and other blood system thromboses. Therefore, strategies to control platelet aggregation and release are desirable in the treatment of these diseases [L. A. Harker and M. Gent, "The Use of Agents that Modify Platelet Function in the Management of Thrombotic Disorders" in *Hemostasis and Thrombosis*, R. W. Colman et al., eds., pp. 1438-56, J. B. Lippincott, Co., Philadelphia, Pa. (1987)]. Furthermore, inhibition of platelet aggregation may also be desirable in the case of extracorporeal treatment of blood, such as in dialysis, storage of platelets in platelet concentrates and following vascular surgery.

A large number of compounds, both naturally occurring and synthetic, are known to cause platelet aggregation and release. These include ADP, collagen, arachidonic acid, epinephrine, thrombin, ristocetin, and the thromboxane $A_2$ mimetic, U46619. The mechanism by which each of these compounds causes platelet aggregation or release varies and involves one of several different receptors on the platelet surface.

A wide variety of antiplatelet agents are currently used for prophylaxis and treatment of arterial thrombotic disorders. Because most of these agents are specific for particular platelet aggregation and/or secretion mechanisms, the agent of choice in a given regimen depends upon the particular mode of platelet activation sought to be inhibited. Antiplatelet agents act in a wide variety of ways, including inhibition of platelet cyclooxygenase, antagonism of the thromboxane $A_2$ receptor, inhibition of thromboxane $A_2$ synthetase, elevation of cAMP levels, and antagonism and neutralization of platelet surface glycoprotein IIb/IIIa.

Glycoprotein IIb/IIIa is the platelet fibrinogen receptor. It self-associates as a two-chain complex in a calcium-dependent manner, upon stimulation of platelets with ADP, epinephrine, thrombin or prostaglandin derivatives and precursors thereof [S. J. Shattil et al., "Changes in the Platelet Membrane Glycoprotein IIb/IIIa Complex During Platelet Activation", *J. Biol. Chem.*, 260, pp. 11107-14 (1985); G. A. Margeurie et al., "Human Platelets Possess an Inducible and Saturable Receptor Specific for Fibrinogen", *J. Biol. Chem.*, 254, pp. 5357-63 (1979)]. This results in platelet aggregation mediated by a cross-linking between fibrinogen and the activated glycoprotein IIb/IIIa complexes of two platelets. Specifically, the glycoprotein IIb/IIIa binds to an Arg-Gly-Asp sequence in fibrinogen [M. D. Pierschbacher and E. Ruoslahti, "Cell Attachment Activity of Fibronectin Can Be Duplicated By Small Synthetic Fragments of the Molecule", *Nature*, 309, pp. 30-33 (1984); K. M. Yamada and D. W. Kennedy, "Dualistic Nature of Adhesive Protein Function: Fibronectin and Its Biologically Active Peptide Fragments Can Autoinhibit Fibronectin Function", *J. Cell Biol.*, 99, pp. 29-36 (1984); N. Ginsberg et al., "Inhibition of Fibronectin Binding to Platelets By Proteolytic Fragments and Synthetic Peptides Which Support Fibroblast Adhesion", *J. Biol. Chem.*, 260, pp. 3931-36 (1985); E. F. Plow et al., "The Effect of Arg-Gly-Asp-Containing Peptides on Fibrinogen and Von Willebrand Factor Binding to Platelets", *Proc. Nat. Acad. Sci. USA*, 82, pp. 8057-61 (1985); T. K. Gartner and J. S. Bennett, "The Tetrapeptide Analogue of the Cell Attachment Site of Fibronectin Inhibits Platelet Aggregation and Fibrinogen Binding to Activated Platelets", *J. Biol. Chem.*, 260, pp. 11891-94 (1985); M. Kloczewiak et al., "Localization of a Site Interacting With Human Platelet Receptor on Carboxy-Terminal Segment of Human Fibrinogen Gamma Chain", *Biochim. Biophys. Res. Comm*, 107, pp. 181-87 (1982)].

The most widely used antiplatelet agent is aspirin, a cyclooxygenase inhibitor. Although aspirin blocks ADP- and collagen-induced platelet aggregation, it fails to prevent cyclooxygenase-independent platelet aggregation initiated by agonists, such as thrombin. Moreover, numerous clinical studies have failed to demonstrate a significant benefit of aspirin in the treatment of arterial thrombosis [L. A. Harker and M. Gent, supra]. In addition, aspirin causes a modification of platelet enzymes that requires at least one week to reverse—effectively putting a treated patient at risk for hemorrhaging if surgery or severe trauma should occur during that one week period.

Specific inhibitors of glycoprotein IIb/IIIa, such as monoclonal antibodies [J. S. Bennett et al., "Inhibition of Fibrinogen Binding to Stimulated Human Platelets By a Monoclonal Antibody", *Proc. Natl. Acad. Sci. USA*, 80, pp. 2417-21 (1983); R. P. McEver et al., "Identification of Two Structurally and Functionally Distinct Sites on Human Platelet Membrane Glycoprotein IIb/IIIa Using Monoclonal Antibodies", *J. Biol. Chem.*, 258, pp. 5269-75 (1983); B. S. Coller, "A New Murine Monoclonal Antibody Reports An Activation-Dependent Change in the Conformation and/or Microenvironment of the Platelet Glycoprotein IIb/IIIa Complex", *J. Clin. Invest.*, 76, pp. 107-08 (1985)] and small Arg-Gly-Asp-containing peptides [T. K. Gartner and J. S. Bennett, supra], are less toxic, faster acting and have a shorter duration of effect as compared to aspirin. These compounds are effective against a number of different platelet aggregation mechanisms, but not against platelet secretion mechanisms. Both Arg-Gly-Asp peptides and antibodies toward glycoprotein IIb/IIIa have been shown to have antithrombotic efficacy in in vivo models of thrombosis [Y. Cadroy et al., "Potent Antithrombotic Effects of Arg-Gly-Asp-Val (RGDV) Peptide In Vivo", *Circulat., Part II*, 75, p. II-313 (1988); B. S. Coller et al., "Antithrombotic Effect of a Monoclonal Antibody to the Platelet Glycoprotein IIb/IIIa Receptor in an Experimental Animal Model", *Blood*, 68, pp. 783-86 (1986); S. R. Hanson et al., "Effects of Monoclonal Antibodies Against the Platelet Glycoprotein IIb/IIIa Complex on Thrombosis and Hemostasis in the Baboon", *J. Clin. Invest.*, 81, pp. 149-58 (1988); T. Yasuda et al., "Monoclonal Antibody Against the Platelet Glycoprotein (GP) IIb/IIIa Receptor Prevents Coronary Artery Reocclusion Following Reperfusing With Recombinant Tissue-Type Plasminogen Activator in Dogs", *J. Clin. Invest.*, 81, pp. 1284-91 (1988); B. S. Coller et al., "Inhibition of Human Platelet Function In Vivo With A Monoclonal Antibody", *Annals Int. Med.*, 109, pp. 635-38 (1988)].

In order to effect inhibition of platelet aggregation, Arg-Gly-Asp-containing peptides must be administered at concentrations greater than $10^{-5}$M. Such requisite dosages imply limited commercial feasibility of those peptides. Monoclonal antibodies to glycoprotein IIb/IIIa are more potent inhibitors of platelet aggregation, but their synthesis in mouse hybridoma cells poses greater potential immunological complications [S. R. Hanson et al., supra]. In addition, Arg-Gly-Asp peptides and antibodies toward glycoprotein IIb/IIIa fail to block platelet secretion. Therefore, these agents may have a limited effectiveness in vivo due to proaggregating effects of released platelet elements and their subsequent activation of the circulating platelet pool.

Thrombin inhibitors, such as heparin, have also been employed as platelet inhibitors. These compounds inhibit or reduce thrombin-mediated platelet aggregation, but have no effect on platelet activation caused by other mechanisms. Furthermore, heparin is known to cause certain dangerous side effects, such as hemorrhaging and thrombocytopenia.

Many attempts to obtain other, more effective antiplatelet agents have centered around snake venoms. Although most snake venoms are known to contain compounds which activate platelets and cause aggregation and secretion, some have been shown to contain inhibitors of platelet aggregation or platelet release reactions as well. Some of these inhibitors, such as those purified from *Agkistrodon rhodostoma* or *Trimeresurus gramineus* are enzymes. These two compounds digest fibrinogen and ADP, respectively [C. Ouyang et al., "γ-Fibrinogenase from *Agkistrodon rhodostoma* (Malayan Pit Viper) Snake Venom", *Toxicon*, 21, pp. 25-33 (1983); C. Ouyang and T. F. Huang, "Inhibition of Platelet Aggregation by 5'-Nucleotidase Purified from *Trimeresurus gramineus* Snake Venom", *Toxicon*, 21, pp. 491-591 (1983)]. Other venom-derived inhibitors act non-enzymatically by blocking the platelet fibrinogen receptor. These include the proteins carinatin, purified from *Echis carinatus* and trigramin, purified from *Trimeresurus gramineus* [C. Ouyang et al., "Characterization of the Platelet Aggregation Inducer and Inhibitor from *Echis carinatus* Snake Venom", *Biochim. Biophys. Acta*, 841, pp. 1-7 (1985); T. F. Huang et al., "Trigramin", *J. Biol. Chem.*, 262, pp. 16157-63 (1987)].

Trigramin is the best known of all of the snake venom-derived inhibitors. It is a single polypeptide chain with a molecular weight of 10,000. It appears to act by blocking the association of fibrinogen and glycoprotein IIb/IIIa (Kd=2.1-8.8×$10^{-8}$M). This inhibition is effectively competed by monoclonal antibodies to glycoprotein IIb/IIIa, as well as by an Arg-Gly-Asp-Ser tetrapeptide. Sequence analysis of a chymotryptic peptide derived from reduced, S-pyridylethyl trigramin reveals that this protein contains an Arg-Gly-Asp sequence. However, whereas small Arg-Gly-Asp containing peptides are effective only in blocking platelet aggregation at concentrations above $10^{-5}$M, trigramin is effective at concentrations of about $10^{-8}$M. It is likely that the increased potency of trigramin stems from an optimized alignment of the Arg-Gly-Asp sequence in three-dimensional space, as well as contributions from other structural determinants in the glycoprotein IIb/IIIa-trigramin complex. Despite its effectiveness, trigramin does not inhibit platelet release reactions, namely serotonin release induced by thrombin or U46619. Therefore, the antiplatelet activity of trigramin in vivo may be impaired due to the proaggregating activities of secreted platelet components, resulting in limited efficacy.

Accordingly, the need still exists for an antiplatelet agent which is free from the drawbacks associated with these conventional compounds. Ideally, this antiplatelet agent should be equally effective in inhibiting all mechanisms of platelet activation and its potency should be such that it can be effectively administered in relatively low doses as compared with dosage regimens using conventional antiplatelet agents.

SUMMARY OF THE INVENTION

The present invention solves the problems referred to above by providing methods for purifying a polypeptide inhibitor of platelet activation and derivatives thereof, from the venom of *Agkistrodon p. piscivorus*. The present invention also provides recombinant DNA molecules characterized by a DNA sequence encoding this polypeptide inhibitor of platelet aggregation alone or fused to a DNA sequence which codes for an antithrombin polypeptide. The invention also relates to hosts transformed with vectors characterized by these recombinant DNA molecules, as well as to the products expressed by these hosts. And the present invention relates to chemically synthesized polypeptide inhibitors of platelet aggregation.

This invention further relates to pharmaceutically acceptable compositions and combinations, and methods utilizing these natural, recombinant or synthetic antiplatelet polypeptides in the treatment of patients and extracorporeal blood. The combinations of the present invention are characterized by other anti-thrombin compounds, such as hirudin or hirudin derivatives. These other anti-thrombin compounds may be present as separate molecules, or, alternatively, conjugated or fused via recombinant DNA techniques to a polypeptide inhibitor of platelet activation according to this invention.

As will be appreciated from the disclosure to follow, the polypeptide inhibitors of platelet activation of the present invention are the most utile compounds of their kind yet to be produced. They are effective in reducing and inhibiting platelet aggregation and platelet secretion caused by various mechanisms. The versatility of the antiplatelet polypeptides of this invention is particularly advantageous, in that the nature of undesired platelet aggregation in a patient or extracorporeal blood need not be determined prior to treatment. This results in a therapy regimen which may be instituted without the inherent delays associated with extensive diagnosis. In addition, the unique properties of the polypeptides of this invention in inhibiting platelet release provides a significant benefit in terms of potency. The efficacy of previously used agents, which cannot block platelet release, is often neutralized by factors released from platelets. Furthermore, because the polypeptides of this invention inhibit the release of thromboxane $A_2$, a potent vasoconstrictor, they possess the unique capability of blocking spasm and stenosis at the site of platelet activation or thrombosis. The recombinant DNA molecules, hosts transformed with them and the products expressed thereby allow the inexpensive and rapid isolation of commercial quantities of the polypeptide inhibitors of platelet aggregation according to this invention.

BRIEF DESCRIPTION OF THE DRAWINGS

FIG. 9 depicts the nucleotide sequence of a synthetic gene encoding a polypeptide inhibitor of platelet activation of this invention.

FIG. 10 depicts 14 individual synthetic oligonucleotides used to construct an intact gene encoding a polypeptide inhibitor of platelet aggregation of this invention.

FIG. 11 depicts the nucleotide sequence of the polylinker region of pNN03.

FIG. 13 depicts the nucleotide sequence of $P_L$-musmc$^{tetR}$.

DETAILED DESCRIPTION OF THE INVENTION

Figure 1:
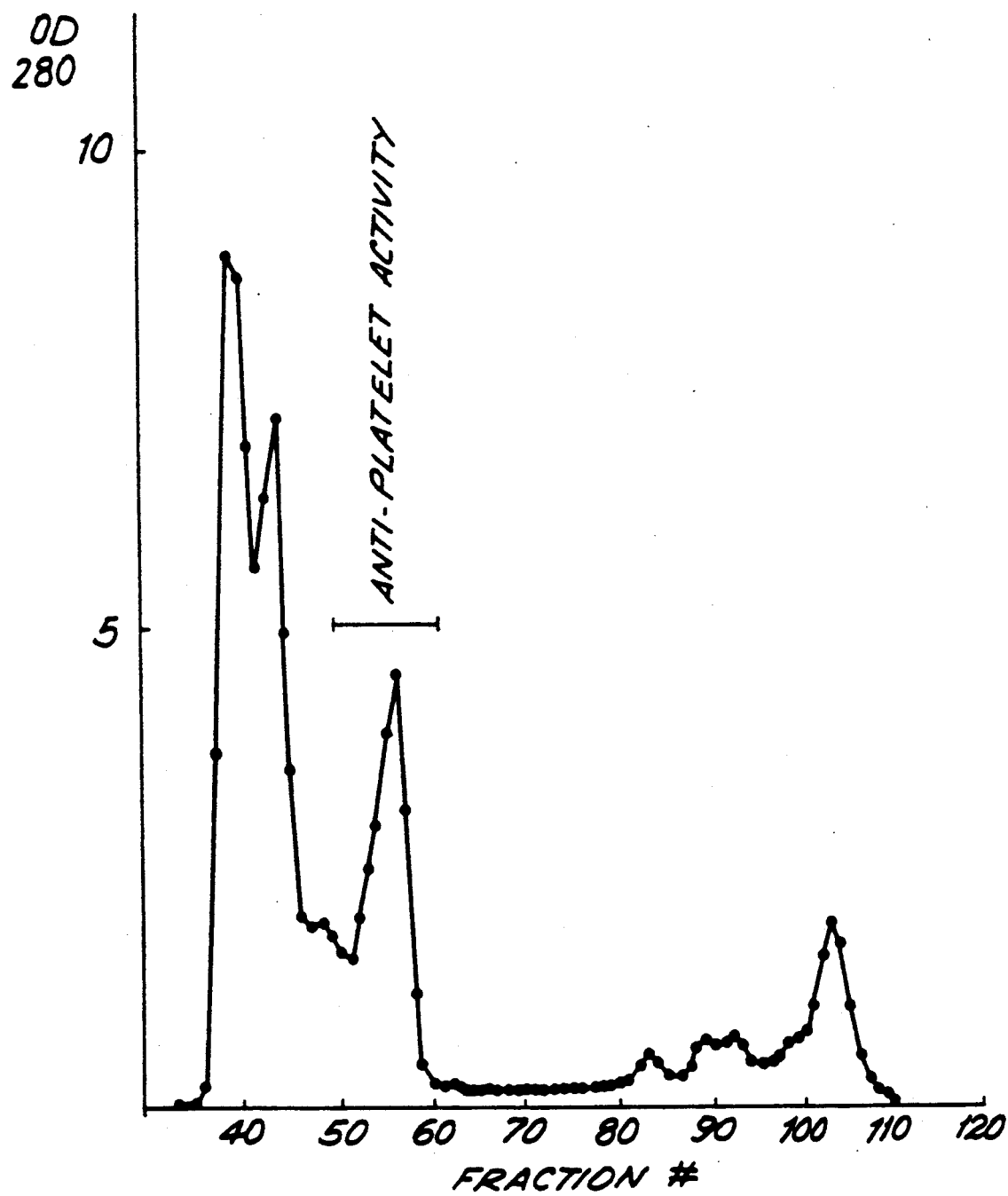
FIG. 1 depicts a chromatogram of a sample of *Agkistrodon p. piscivorus* venom fractionated on a Sephadex G-50 column.

Throughout the specification and in the claims, the terms "polypeptide inhibitors of platelet activation" and "antiplatelet polypeptides" are used interchangeably and refer to polypeptides which inhibit both platelet aggregation and platelet release reactions.

The present invention relates to methods for purifying polypeptide inhibitors of platelet activation, or derivatives thereof, from snake venom. Specifically, the venom is obtained from the American Water Moccasin (*Agkistrodon p. piscivorus*). The venom may be obtained by directly milking the live snake, or, more preferably, as a lyophilized preparation from a commercial source.

Once the venom is obtained, it is dissolved or diluted into an aqueous buffer. Any aqueous buffer with a buffering capacity of between about pH 2–10 may be employed. These buffers are well known in the art. Most preferably, the buffer is Tris-HCl with a pH of about 7.4. The chosen buffer may optionally contain a salt, preferably NaCl, at a concentration of between about 0.001M and 1.0M. It is also desirable that the buffer contains one or a combination of protease inhibitors, to prevent possible degradation of the desired polypeptide by native proteases present in the venom. The choice of protease inhibitors may be made from any of a large number of well-known compounds. These include, but are not limited to, PMSF, leupeptin, soybean trypsin inhibitor, pepstatin, EDTA, EGTA and DFP.

After solubilization, any undissolved material should be removed prior to chromatography. This may be achieved by filtration, or most preferably, by centrifugation. The remaining soluble material is then fractionated away from other molecules having dissimilar molecular weights by molecular sizing means. Any of the numerous molecular sizing techniques known in the art may be used in the methods of this invention. Preferably, molecular sizing will be achieved by gel chromatography. The choice of resin used for gel chromatography should be such that the polypeptide, which is approximately 18,000 daltons, elutes in the included volume. Preferred resins are, for example, Sephadex G-75, Sephadex G-50, Biogel P-30, Biogel P-60 and Sephacyl S-100. Most preferred is Sephadex G-50. Whatever resin is employed, it should be equilibrated in the identical buffer used to dissolve the venom (but without protease inhibitors) prior to chromatography. The same buffer should also be used during chromatography.

The flow rate of the solution through the chromatography resin and the size of the fractions collected should be adjusted to provide maximum separation efficiency within a minimum amount of time. These adjustments are well-known by those skilled in the art.

Fractions containing a polypeptide inhibitor of platelet activation may be identified by biological activity or reaction with specific antibodies. Any of a number of well-known assays may be employed for this purpose. These assays include, but are not limited to, ELISA, radioimmunoassay, inhibition of platelet aggregation or secretion, platelet binding, and competition of ligand binding to platelets. Preferably, the assay will be one that may be performed in a short period of time, in order to avoid any degradation due to storage of the fractions over excessive time periods. Preferred assays measure inhibition of collagen-induced platelet aggregation in a sample of human platelets. The most preferred assay is one which utilizes an automated assay system, such as a Bio-Data 4-channel Aggregometer [Hatboro, Pa.].

Once identified, the fractions containing antiplatelet activity are pooled. The choice of endpoint fractions to pool will be based on a balancing of factors known to those skilled in the art. These factors include maximizing the amount of activity in the pool, while minimizing the amount of contaminating protein. The pooled fractions are then contacted with an ion-exchange resin. This may be performed in a batch-wise manner, or more preferably, by column chromatography. Although any anion or cation exchange resin may be utilized in the purification methods of this invention, cation resins are preferred. The choice of particular cation resin will be based on its cost, binding capacity, flow rate and other factors known to those skilled in the art. Examples of cation resins that may be employed in the methods of this invention include CM-52, CM-Sepharose, CM-Sephadex, S-Sephadex and S-Sepharose. According to a preferred embodiment of the present invention, the cation resin used is S-Sepharose (fast-flow).

Whatever resin is employed, it should be equilibrated in an appropriate buffer prior to being contacted with the antiplatelet polypeptide-containing sample. The chosen buffer preferably is identical to the buffer utilized in the previous gel chromatography step, in order to avoid any intermediate buffer exchange steps. To maximize the speed and economy of the purification method, the chosen resin is one which preferably will not bind the antiplatelet polypeptide under these initial buffer conditions. In this manner, contaminating polypeptides, specifically phospholipase $A_2$, are adsorbed away from the desired antiplatelet polypeptide. The flow-through from the ion exchange step is pooled and may be stored at about 4° C. until further use. It should be obvious to those in the art that the order of the chromatography steps (i.e., molecular sizing followed by ion-exchange, or vice versa) may be reversed. Therefore, an alternate embodiment of this invention employs ion-exchange prior to molecular sizing.

The final step of the purification according to the methods of this invention is reverse phase HPLC. A variety of reverse phase HPLC resins may be employed in this step. These include disilyl, tetrasilyl, octasilyl and octadecylsilyl supports. The most preferred resin is tetrasilyl. The buffer system utilized in this step preferably consists of a linear gradient of increasing acetonitrile concentration in 0.1% trifluoroacetic acid (TFA). However, any buffer system that effectively purifies the antiplatelet polypeptide away from remaining contaminants at this step may be utilized. These alternate buffer systems are known in the art. The column effluent is continuously monitored for absorbance at 214 nm and 280 nm. Peak absorbing fractions are evaporated and redissolved in water prior to assaying for the antiplatelet polypeptide as described above.

We believe that polypeptides with a structure and biological activity similar to that of the inhibitor of platelet activation isolated from the North American Water Moccasin are naturally present in the venoms of other New World snakes. Accordingly, the purification methods of the present invention are also applicable to these other polypeptides.

In addition, the purification methods of this invention are useful to isolate proteolytic fragments of antiplatelet polypeptides which retain the biological activity of the intact polypeptide derived from either the North American Water Moccasin or another New World snake (see particularly, Example 1). Such proteolytic fragments may occur naturally or artifactually as a result of the purification process.

The present invention also relates to polypeptide inhibitors of platelet activation purified by the above process and their use in pharmaceutically acceptable compositions and methods for decreasing or preventing platelet aggregation and release reactions.

This invention also relates to recombinant and synthetically produced polypeptide inhibitors of platelet activation and their use in pharmaceutically acceptable compositions, combinations and methods for decreasing or preventing platelet aggregation and release reactions.

According to one embodiment of this invention, any of the above-described compositions and methods are useful in treating patients or extracorporeal blood. As used in this application, the term "extracorporeal blood" includes blood removed in line from a patient, subjected to extracorporeal treatment, and returned to the patient in processes such as dialysis procedures or blood filtration or blood bypass during surgery. The term also includes blood products which are stored extracorporeally for eventual administration to a patient. Such products include whole blood, platelet concentrates and any other blood fraction in which inhibition of platelet aggregation and platelet release is desired. The term "patient" as used herein means any mammal, especially humans.

According to an alternate embodiment, the present invention relates to combinations for decreasing or preventing platelet aggregation and release and methods which employ them. These combinations may contain a variety of other antiplatelet or anti-thrombin compounds in addition to a naturally purified, recombinant or synthetic polypeptide inhibitor of platelet activation of this invention. Preferred anti-thrombin compounds are hirudin derivatives. For the purposes of this application, the term "hirudin derivative" means any peptide which is 100% homologous to any segment of the amino acid sequence of hirudin and which displays antithrombin activity [see, for example, U.S. patent application Ser. No. 164,178, the disclosure of which is incorporated herein by reference]. The term also includes full-length hirudin. Most preferred are hirudin, Sulfo-Tyr$_{63}$hirudin$_{53-64}$ and Sulfonyl-Tyr$_{63}$hirudin$_{53-64}$.*

*Sulfo-Tyr$_{63}$hirudin$_{53-64}$ is a carboxy terminal dodecapeptide of hirudin having the amino acid sequence Asn-Gly-Asp-Phe-Glu-Glu-Ile-Pro-Glu-Glu-Tyr(OSO$_3$)-Leu. Its synthesis is described in copending U.S. patent application Ser. No. 164,178. Sulfonyl-Tyr$_{63}$hirudin$_{53-64}$ is a carboxy terminal dodecapeptide of hirudin having the formula Asn-Gly-Asp-Phe-Glu-Glu-Ile-Pro-Glu-Glu-Tyr(SO$_3$)-Leu. Its synthesis is described on copending U.S. patent application Ser. No. 251,150, the disclosure of which is incorporated herein by reference. The synthesis of both of these compounds may be achieved by conventional methods.

As used herein, the term "combination" denotes a single dosage form, wherein a polypeptide inhibitor of platelet activation of this invention may be chemically conjugated to another platelet inhibitor polypeptide or to an anti-thrombin polypeptide. It alternatively denotes a single dosage form which contains the polypeptide inhibitor of platelet activation and the other polypeptide in the same composition, but as separate compounds. And, the term "combination" alternatively denotes multiple dosage forms wherein the polypeptide inhibitor of platelet activation and the other polypeptide are administered separately, but concurrently, or wherein the two agents are administered sequentially.

The cross-linking of the polypeptide inhibitor of platelet activation to an anti-thrombin polypeptide, such as a hirudin derivative, may be carried out by chemical cross-linking methods well known in the art. Most preferably, such combinations are formed by cross-linking a natural or recombinant polypeptide inhibitor of platelet activation to a synthetic hirudin derivative. To achieve such a combination, the hirudin derivative may be synthesized with a cross-linking moiety, such as dinitrofluorobenzene, at its $NH_2$ terminus. Alternatively, the hirudin derivative may be conjugated to a natural or recombinant polypeptide inhibitor of platelet activation by the use of agents such as glutaraldehyde, dimethyladipimidate, or any other bifunctional cross-linkers known in the art. The conjugation may involve a 1:1 stoichiometry, or a higher ratio of hirudin derivative to the recombinant polypeptide.

The present invention relates to synthetic polypeptides of platelet activation. Such synthetic antiplatelet polypeptides may be prepared by conventional chemical synthesis techniques, for example, synthesis on a solid support.

The present invention also relates to recombinant and synthetic DNA molecules which encode polypeptide inhibitors of platelet activation. The synthesis of these DNA molecules may be achieved by methods well known in the art. For example, these recombinant DNA molecules may be isolated from a *Agkistrodon p. piscivorus* venom gland cDNA library. The synthesis of cDNA libraries and the choice of vector into which the cDNA molecules may be cloned are conventional techniques [T. Maniatis et al., "Molecular Cloning - A Laboratory Manual", Cold Spring Harbor (1982)].

A wide variety of methods may be used in locating and identifying cDNA sequences corresponding to a polypeptide inhibitor of platelet activation of this invention. The two most preferred techniques are the use of oligonucleotide probes based on the amino acid sequence of the antiplatelet polypeptide and immunoscreening, which utilizes antibodies against the antiplatelet polypeptide to detect clones which express cDNA sequences corresponding to an antiplatelet polypeptide. It will be obvious to those of skill in the art that the choice of oligonucleotides probes will be based upon those stretches of amino acids which are encoded by the least redundant DNA sequences. The immunoscreening technique requires that the cDNA library be contained in a vector capable of expression.

Such vectors include lambda gt11, lambda gt10 and other expression vectors known in the art. Antibodies employed in the immunoscreening technique include antibodies against intact polypeptide inhibitors of platelet activation, antibodies against denatured polypeptide inhibitors of platelet activation and antibodies against peptide portions of polypeptide inhibitors of platelet activation. Once an antiplatelet polypeptide cDNA has been identified and isolated, it may be removed from the vector and analyzed to determine whether it contains the entire antiplatelet polypeptide coding sequence. Partial cDNAs may themselves be used to reprobe the cDNA library and to locate full-length cDNAs.

More preferably, the DNA molecules of this invention may be synthesized from oligonucleotides by chemical means using an oligonucleotide synthesizer. Such oligonucleotides may be designed based on the disclosed amino acid sequence of the antiplatelet polypeptide.

Standard methods may be applied to synthesize a gene encoding a polypeptide inhibitor of platelet activation. For example, the complete amino acid sequence may be used to construct a back-translated gene. A DNA oligomer containing a nucleotide sequence capable of coding for the desired polypeptide inhibitor of platelet activation may be synthesized in a single step. Alternatively, several smaller oligonucleotides coding for portions of the antiplatelet polypeptide may be synthesized and subsequently ligated together. Preferably, the antiplatelet polypeptide gene is synthesized as 10–20 separate oligonucleotides which are subsequently linked together. The individual oligonucleotides contain 5' or 3' overhangs for complementary assembly.

Following synthesis of the oligomers and cleavage of the desired vector, assembly of the antiplatelet polypeptide gene may be achieved in one or more steps by techniques well known in the art. Once assembled, the gene will be characterized by sequences which are recognized by restriction endonucleases, including unique restriction sites for direct assembly into a cloning or an expression vector; preferential codons based upon the host expression system to be used; and a sequence which, when transcribed, produces a mRNA with minimal secondary structure. Proper assembly may be confirmed by nucleotide sequencing, restriction mapping, and expression of a biologically active antiplatelet polypeptide in a suitable host.

It will be understood by those of skill in the art that, due to the degeneracy of the genetic code, many different synthetic DNAs will be capable of encoding the polypeptide inhibitors of platelet activation of this invention. It will also be apparent that many of these DNAs will be faithfully expressed in host transformed with them. Therefore, the present invention relates to not only one, but all DNA molecules which encode the desired antiplatelet polypeptide and which can be expressed by one or more hosts transformed with them. Most of these DNA molecules will be capable of hybridizing to one another under moderately stringent conditions. These conditions are known to those of skill in the art and are exemplified by 1X SSC at 42° C., followed by washing at a somewhat higher stringency such as 0.1X–1X SSC at 58° C.

According to another embodiment, the recombinant DNA molecules of this invention encode novel fusion proteins comprising a polypeptide inhibitor of platelet activation and an anti-thrombin polypeptide, preferably a hirudin derivative. The DNA sequence which encodes hirudin is known and may be obtained by a variety of conventional techniques [C. Bergmann et al., "Chemical Synthesis and Expression of a Gene Coding for Hirudin, the Thrombin-Specific Inhibitor from the Leech *Hirudo medicinalis*", *Biol. Chem. Hoppe-Seyler*, 367, pp.731–40 (1986); E. Fortkamp et al., "Cloning and Expression in *Escherichia coli* of a Synthetic DNA for Hirudin, the Blood Coagulation Inhibitor in the Leech", DNA, 5, pp. 511–17 (1986)].

Once the DNA encoding the polypeptide inhibitor of platelet activation and the DNA encoding the hirudin derivative have been obtained or synthesized, the two DNAs may be ligated together to produce a DNA encoding a single fusion protein. It should be understood that the ligation must be performed so that the reading frame continues undisturbed from the DNA encoding the polypeptide inhibitor of platelet activation into the hirudin derivative DNA, or vice versa, depending on the ligation. Therefore, the two DNA sequences optionally may be bridged by a linker which does not destroy the integrity of the reading frame of either DNA. Such linkers are well known in the art and may additionally encode a unique restriction site. Achievement of proper fusions will employ methods well known in the field of molecular biology. These fusion proteins may be employed in pharmaceutically effective compositions according to this invention.

The DNA sequences and recombinant DNA molecules of the present invention may be inserted into and expressed using a wide variety of vectors. For example, useful vectors may consist of segments of chromosomal, non-chromosomal and synthetic DNA sequences, such as various known derivatives of SV40 and known bacterial plasmids, e.g., plasmids from *E.coli* including colE1, pCR1, pBR322, pMB9 and RP4; phage DNAs, e.g., the numerous derivatives of λ phage, e.g., NM 989, and other DNA phages, e.g., M13 and other *Filamentous* single-stranded DNA phages; vectors useful in yeasts, such as the 2 μm plasmid; vectors useful in animal cells, such as those containing SV40 adenovirus and retrovirus-derived DNA sequences; and vectors derived from combinations of plasmids and phage DNAs, such as plasmids which have been modified to employ phage DNA or other derivatives thereof.

Such expression vectors are also characterized by at least one expression control sequence that may be operatively linked to the polypeptide inhibitor of platelet activation or fusion protein DNA sequence inserted in the vector in order to control and to regulate the expression of that cloned DNA sequence. Examples of useful expression control sequences include the lac system, the trp system, the tac system, the trc system, major operator and promoter regions of phage λ, the control region of fd coat protein, the glycolytic promoters of yeast, e.g., the promoter for 3-phosphoglycerate kinase, the promoters of yeast acid phosphatase, e.g., Pho5, the promoters of the yeast-mating factors, and promoters derived from polyoma, adenovirus, retrovirus, and simian virus, e.g., the early and late promoters of SV40, and other sequences known to control the expression of genes of prokaryotic or eukaryotic cells and their viruses or combinations thereof.

Among such useful expression vectors are vectors that enable the expression of the cloned polypeptide inhibitor of platelet activation in eukaryotic hosts, such as animal and human cells [e.g., P. J. Southern and P. Berg, *J. Mol. Appl. Genet.*, 1, pp. 327–41 (1982); S. Subramani et al., *Mol. Cell. Biol.*, 1, pp. 854–64 (1981); R. J. Kaufmann and P. A. Sharp, "Amplification And Expression Of Sequences Cotransfected with A Modular Dihydrofolate Reductase Complementary DNA Gene", *J. Mol Biol.*, 159, pp. 601–21 (1982); R. J. Kaufmann and P. A. Sharp, *Mol. Cell. Biol.*, 159, pp. 601–64 (1982) S. I. Scahill et al., "Expression And Characterization Of The Product Of A Human Immune Interferon DNA Gene In Chinese Hamster Ovary Cells", *Proc. Natl. Acad. Sci. USA*, 80, pp. 4654–59 (1983); G. Urlaub and L. A. Chasin, *Proc. Natl. Acad. Sci. USA*, 77, pp. 4216–20 (1980)].

Furthermore, within each specific expression vector, various sites may be selected for insertion of DNA sequences encoding a polypeptide inhibitor of platelet activation or an antiplatelet polypeptide-containing fusion protein of this invention. These sites are usually designated by the restriction endonuclease which cuts them. They are well recognized by those of skill in the art. It is, of course, to be understood that an expression vector useful in this invention need not have a restriction endonuclease site for insertion of the chosen DNA fragment. Instead, the vector may be joined to the fragment by alternative means.

The expression vector, and in particular the site chosen therein for insertion of a selected DNA fragment and its operative linking therein to an expression control sequence, is determined by a variety of factors, e.g., number of sites susceptible to a particular restriction enzyme, size of the protein to expressed, susceptibility of the desired protein to proteolytic degradation by host cell enzymes, contamination or binding of the protein to be expressed by host cell proteins difficult to remove during purification, expression characteristics, such as the location of start and stop codons relative to the vector sequences, and other factors recognized by those of skill in the art. The choice of a vector and an insertion site for a DNA sequence is determined by a balance of these factors, not all selections being equally effective for a given case.

Useful hosts which may be transformed with these vectors and which may be employed to express the polypeptides of this invention may include well known eukaryotic and prokaryotic hosts, such as strains of *E.coli*, such as *E.coli* SG-936, *E.coli* HB 101, *E.coli* W3110, *E.coli* X1776, *E.coli* X2282, *E.coli* DHI, and *E.coli* MRCl, *Pseudomonas, Bacillus*, such as *Bacillus subtilis, Streotomvces*, yeasts and other fungi, animal cells, such as COS cells and CHO cells, human cells, insect cells and plant cells in tissue culture.

Of course, not all host/expression vector combinations will function with equal efficiency in expressing the DNA sequences of this invention or in producing the polypeptide inhibitor of platelet activation or fusion polypeptide. However, a particular selection of a host-expression vector combination may be made by those of skill in the art, after due consideration of the principles set forth herein without departing from the scope of this invention. For example, the selection should be based on a balancing of a number of factors. These include, for example, compatibility of the host and vector, toxicity of the proteins encoded by the DNA sequence to the host, ease of recovery of the desired protein, expression characteristics of the DNA sequences and the expression control sequences operatively linked to them, biosafety, costs and the folding, form or any other necessary post-expression modifications of the desired protein.

We believe that the critical structural feature of the antiplatelet polypeptides of the present invention is their dimeric form, each polypeptide member of the dimer having an Arg-Gly-Asp sequence that is capable of binding to the platelet surface. The phrase "capable of binding" as used herein denotes that the Arg-Gly-Asp sequence is situated so that its binding to the platelet surface is not sterically hindered. We also believe that any polypeptide or semi-peptidic molecule that contains these structural features will be capable of inhibiting platelet aggregation and release. Accordingly, the present invention also relates to other inhibitors of platelet activation which contain this salient structural feature in addition to the recombinant polypeptides.

Such other inhibitors of platelet activation may be polypeptides containing deletions or amino acid modifications from the authentic antiplatelet polypeptide.

These may be made by appropriate construction on the DNA level, by direct synthesis at the polypeptide level, or by chemical or enzymatic reaction of the authentic polypeptide. Alternatively, these other inhibitors of platelet activation may be semi-peptidic and may be synthesized by standard organic chemistry procedures. All of these compounds will be effective antiplatelet agents. The synthesis of these alternative molecules permits the production of commercially feasible quantities of antiplatelet compounds. Moreover, these alternate antiplatelet compounds may be designed in such a manner so as to enhance the desired biological activity.

The pharmaceutically acceptable compositions and combinations of the present invention preferably include at least one pharmaceutically acceptable carrier. In addition, the pharmaceutically acceptable compositions and combinations of the present invention also comprise a pharmaceutically acceptable buffer, preferably phosphate buffered saline, together with a pharmaceutically acceptable compound for adjusting isotonic pressure, such as sodium chloride, mannitol or sorbitol.

Such compositions are suitably adapted for oral, parenteral and topical administration, parenteral compositions being most preferred. Compositions formulated for topical administration may, for example, be in aqueous jelly, oily suspension or emulsified ointment form. For parenteral administration, fluid unit dose forms may be prepared containing a composition or combination of the present invention and a sterile vehicle. The polypeptides contained in the pharmaceutically acceptable composition or combination may be either suspended or dissolved, depending on the nature of the vehicle employed. Parenteral compositions are normally prepared by dissolving the polypeptides, optionally together with other components, in a vehicle and filter sterilizing before filling into a suitable vial or ampule and sealing. Preferably, adjuvants such as a local anesthetic, preservatives and buffering agents may also be dissolved in the vehicle. The composition may then be frozen and lyophilized to enhance its stability.

Parenteral suspensions are prepared in substantially the same manner, except that the polypeptides are suspended, rather than dissolved in the vehicle. Sterilization of the polypeptides and other optional components is achieved preferably by exposure to ethylene oxide before suspension in the sterile vehicle. Advantageously, a pharmaceutically acceptable surfactant or wetting agent is included in the composition to facilitate uniform distribution of the polypeptide and any other optional components.

Tablets and capsules for oral administration may contain conventional excipients such as binding agents, fillers, diluents, tabletting agents, lubricants, disintegrants, colorants, flavorings and wetting agents. The tablet may be coated according to methods well known in the art.

Suitable fillers for use include cellulose, mannitol, lactose and other similar agents. Suitable disintegrants include, but are not limited to, starch, polyvinylpyrrolidone and starch derivatives such as sodium starch glycollate. Suitable lubricants include, for example, magnesium stearate. Suitable wetting agents that are useful include sodium lauryl sulfate.

Oral liquid preparations may be in the form of aqueous or oily suspensions, solutions, emulsions, syrups or elixirs, or may be presented as a dry product for reconstitution with water or other suitable vehicle before use. Such liquid preparations may contain conventional additives. These include suspending agents, such as sorbitol, syrup, methyl cellulose, gelatin, hydroxyethylcellulose, carboxymethylcellulose, aluminum stearate gel or hydrogenated edible fats; emulsifying agents which include lecithin, sorbitan monooleate or acacia; non-aqueous vehicles, such as almond oil, fractionated coconut oil, and oily esters; and preservatives, such as methyl or propyl p-hydroxybenzoate or sorbic acid.

For administration by injection, a therapeutic amount of a natural, recombinant or synthetic polypeptide inhibitor of platelet activation will normally be in the dosage range of between about 0.01-100 mg/kg body weight, preferably about 0.1-50 mg/kg body weight. For the treatment of extracorporeal blood, the antiplatelet polypeptides of the present invention should be used at about 0.05-10 $\mu$g/ml, preferably at about 0.5-5 $\mu$g/ml of extracorporeal blood. Effective combinations according to the present invention will contain between about 0.01-100 mg/kg body weight, preferably about 0.1-50 mg/kg body weight of a natural, recombinant or synthetic polypeptide inhibitor of platelet activation and between about 0.01-100 mg/kg body weight, preferably about 0.1-50 mg/kg of another antiplatelet or anti-thrombin agent. For treatment of extracorporeal blood using the combinations of this invention, both the polypeptide inhibitor of platelet activation and the other anti-platelet or anti-thrombin agent should be used at about 0.05-10 $\mu$g/ml, preferably at about 0.5-5 $\mu$g/ml of extracorporeal blood. It should be understood that other dosages outside of these illustrative ranges may be employed in the pharmaceutical compositions and combinations of this invention.

According to another embodiment of this invention, a natural, recombinant or synthetic polypeptide inhibitor of platelet activation of this invention may be formulated in compositions and methods for coating the surfaces of invasive devices, resulting in lower risk of platelet activation in patients receiving such devices. Alternatively, combinations comprising an antiplatelet polypeptide of this invention and an anti-thrombin agent may be employed. Surfaces that may be coated according to the methods, combinations and compositions of this invention are exemplified by those of prostheses, artificial valves, vascular grafts, stents and catheters. Methods and compositions for coating these devices are known to those of skill in the art. These include chemical cross-linking or physical adsorption of the antiplatelet polypeptide-containing compositions to the surfaces of the devices.

In order that this invention may be more fully understood, the following examples are set forth. It should be understood that these examples are for illustrative purposes only and are not to be construed as limiting this invention in any manner.

EXAMPLE 1

Purification Of A Polypeptide Inhibitor Of Platelet Activation

We dissolved 0.5 g of lyophilized venom from *Agkistrodon p. piscivorus* [Miami Serpentarium Laboratories, Salt Lake City, Utah] in 10 ml of 0.025M Tris-HCl, pH 7.5, containing 1 mM EDTA and 1 mM PMSF at room temperature. We then removed any insoluble material by centrifuging the venom solution at 3,000 rpm for 10 minutes. We next applied the supernatant to a column (2.5 cm×90 cm) of Sephadex G-50 (Sigma, St. Louis, Mo.) which had previously been equilibrated in 0.025M Tris-HCl, pH 7.5, containing 1 mM EDTA. We collected fractions of 5 ml. Fractions were assayed for protein content by measuring their absorbance at 280 nm. We also assayed aliquots of each fraction for antiplatelet activity using fresh, human platelet-rich plasma (0.5 ml) and collagen (1 μg/ml) in a Biodata 4-channel Aggregometer according to manufacturer's directions. FIG. 1 depicts the chromatographic profile from Sephadex G-50. Phospholipase $A_2$ is also known to coelute with the antiplatelet polypeptide at this step [J. M. Maraganore et al., "A New Class of Phospholipases $A_2$ With Lysine in Place of Aspartate 49", *J. Biol. Chem.*, 259, pp. 13839–43 (1984)].

Fractions containing antiplatelet activity were pooled and then applied to a 75 ml column of S-Sepharose fast flow (Sigma). The S-Sepharose column had previously been equilibrated in 0.025M Tris-HCl, pH 7.5. After the Sephadex G-50 pool was applied to the cation exchange resin, we washed the column in equilibration buffer until the absorbance of the effluent at 280 nm remained constant. The antiplatelet activity was contained in the effluent. This cation exchange step facilitated purification by adsorbing out contaminating proteins, such as phospholipase $A_2$. If necessary, we stored the effluent at 4° C. until further use.

Figure 2:
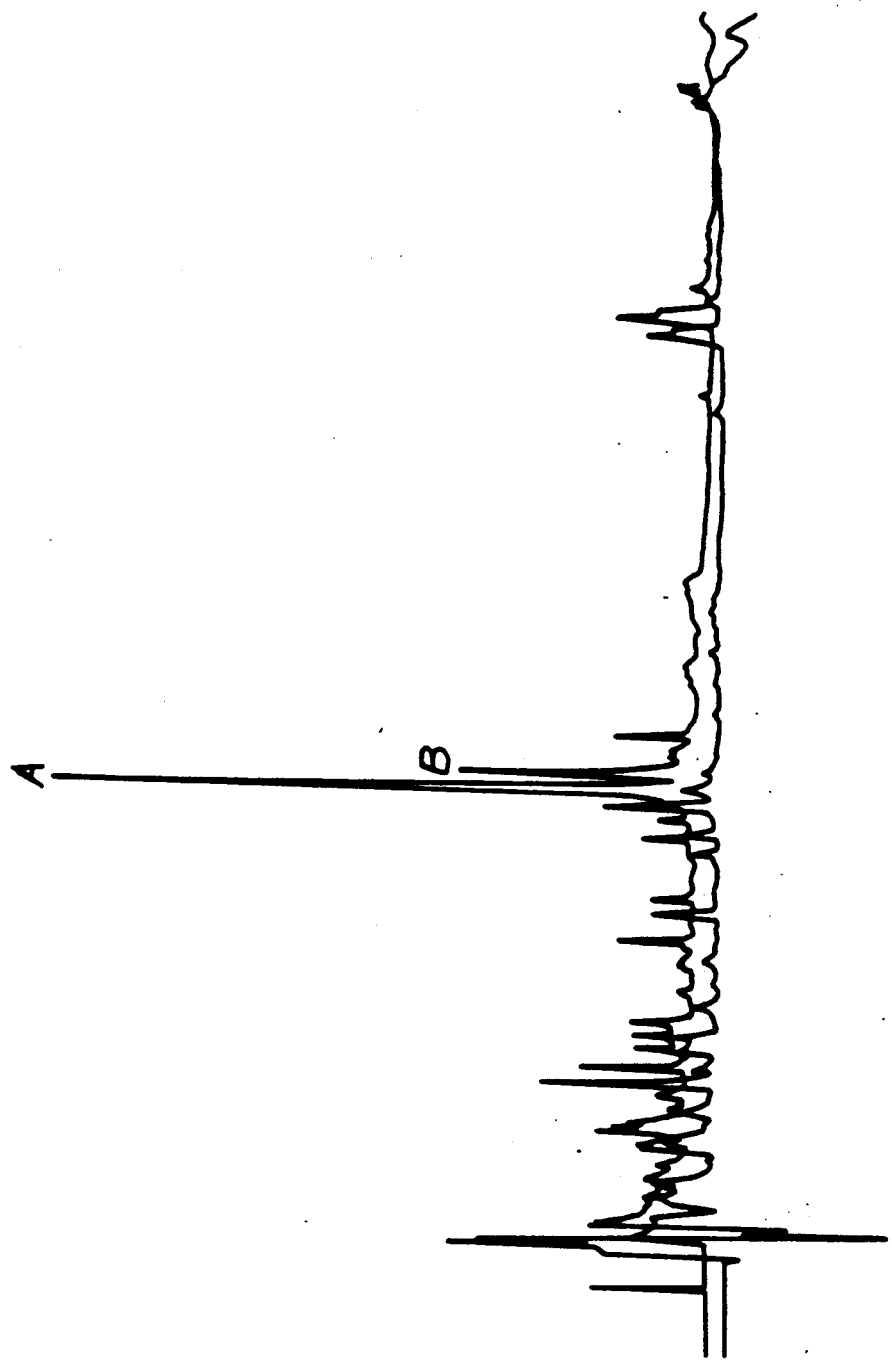
FIG. 2 depicts a chromatogram of a partially purified sample of a polypeptide inhibitor of platelet activation of this invention fractionated on a Vydac C4 reverse phase HPLC column.

As a final purification step, we applied 0.5 ml aliquots of the S-Sepharose effluent to a 0.46 cm ×25 cm Vydac C4 reverse phase HPLC column. HPLC was performed using an Applied Biosystems 150 A liquid chromatographic system (Foster City, Calif.). We had previously equilibrated the C4 column in 0.1% TFA in water. The column was developed with a linear gradient (0–30%) of increasing acetonitrile in 0.1% TFA over 60 minutes at a flow rate of 1.0 ml/minute. The effluent stream was monitored at 214 nm and 280 nm. We collected 0.5 ml fractions, dried them in a Speed-Vac instrument (Savant; Hicksville, N.Y.) and redissolved them in 0.1 ml water. The fractions were then tested for antiplatelet activity as described previously. We found a major, well-resolved peak eluting at 12% acetonitrile, which contained antiplatelet activity (FIG. 2, peak A). This peak corresponded to an intact, purified polypeptide inhibitor of platelet activation. We also found a smaller, minor peak which also contained antiplatelet activity (FIG. 2, peak B). The latter peak was shown to contain the identical 41 $NH_2$-terminal amino acids as the former peak. We believe this latter peak represents a C-terminal proteolyzed form of the antiplatelet polypeptide. Purification of intact the antiplatelet polypeptide by this method yielded 3 mg of polypeptide per gram of venom.

EXAMPLE 2

Structural Studies of The Polypeptide Inhibitor Platelet Activation

Figure 3:
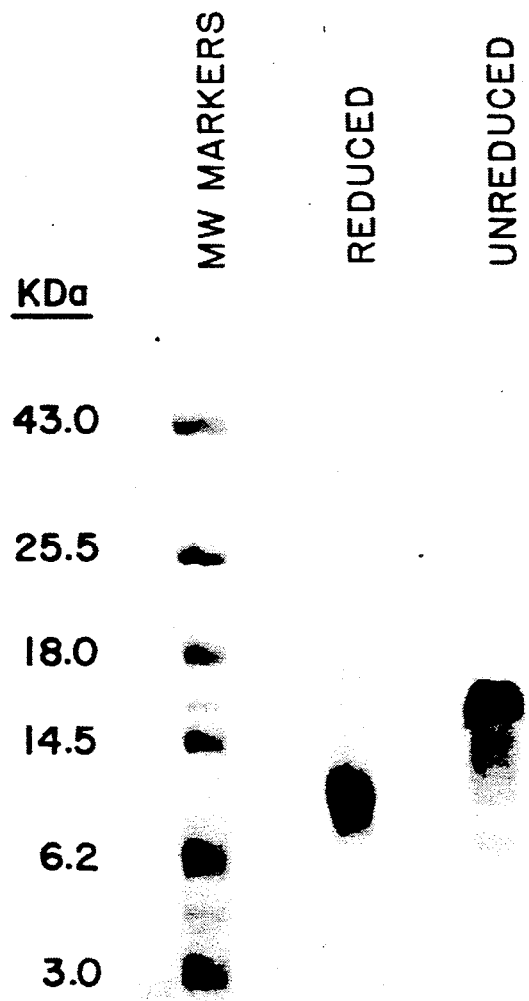
FIG. 3 depicts an SDS-polyacrylamide gel of each of a reduced and an unreduced polypeptide inhibitor of platelet activation of this invention.

We performed SDS-polyacrylamide gel electrophoresis on the purified polypeptide inhibitor of platelet activation as prepared in Example 1 under both reducing and non-reducing conditions (FIG. 3). More specifically, we electrophoresed the protein in 19% polyacrylamide gels in the presence or absence of β-mercaptoethanol and visualized the protein by Coomassie Blue staining. Under non-reducing conditions, the antiplatelet polypeptide migrated with an apparent molecular weight of 18,000 daltons. In the presence of a reducing agent, the antiplatelet polypeptide was found to migrate with an apparent molecular weight of 9,000 daltons. This data indicates that the polypeptide inhibitor of platelet activation exists in nature as a dimer. It should be noted that the polypeptide stained poorly with Coomassie Blue and that adequate visualization required the presence of at least 10–20 μg.

We performed amino acid analysis of the antiplatelet polypeptide by first hydrolyzing the protein in 6 N HCl at 110° C. for 24 hours, in vacuo. The hydrolyzates were then analyzed by ion-exchange chromatography and post-column ninhydrin derivatization employing a Beckman System 6300 Amino Acid Analyzer (Palo Alto, Calif.). Amino acid analysis revealed a high content of cysteine (21.1%) and proline (9.2%). We also noted a complete lack of tryptophan in the antiplatelet polypeptide molecule. The complete results of the amino acid analysis, showing molar % of each amino acid, are given below:

| Asp | 13.3 | Thr | 2.2 | Ser | 1.7 |
|---|---|---|---|---|---|
| Glu | 9.9 | Gly | 10.9 | Ala | 9.0 |
| Cys | 21.1 | Val | 2.7 | Met | 0.9 |
| Ile | 1.2 | Leu | 2.6 | Pro | 9.2 |
| Tyr | 1.1 | Phe | 2.5 | His | 1.4 |
| Lys | 3.9 | Trp* | 0.0 | Arg | 6.4 |

*Determined by the absence of absorbance at 280 nm by UV spectral analysis.

Determined by the absence of absorbance at 280 nm by UV spectral analysis.

Prior to amino acid sequence determination, an aliquot of the intact antiplatelet polypeptide was modified by reduction and S-pyridylethylation of the half cysteines (RPE-antiplatelet polypeptide). Specifically, 0.1 mg of antiplatelet polypeptide was denatured in 0.5 ml of 0.1M Tris-HCl, pH 8.0, 6M guanidinium chloride and 1 mM EDTA. We added 15 μl of β-mercaptoethanol to this solution and incubated for 2 hours at room temperature under a gentle stream of $N_2$. We then added 100 μl of vinyl pyridine to the solution. The mixture was then capped and allowed to stand for 30 minutes in the dark. We stopped the reaction by adding 10 μl of β-mercaptoethanol and dialyzing the solution against 10 volumes of 1% acetic acid. Following dialysis, the RPE-antiplatelet polypeptide was lyophilized and stored as a powder at 4° C. until further use.

We also modified another aliquot of the antiplatelet polypeptide by reduction and S-carboxymethylation of the half-cysteine residues (RCM-antiplatelet polypeptide). For this reaction, we dissolved 0.1 mg of the antiplatelet polypeptide in 0.5 ml of 0.1M Tris-HCl, pH 8.0, 6M guanidinium chloride and 1 mM EDTA. The remainder of the reaction steps were carried out in a standard manner [C. H. W. Hirs, "Reduction and S-Carboxymethylation of Proteins", in *Methods In Enzymol.*, XI, pp. 199–203 (1967)].

Amino terminal amino acid sequence analysis was performed by automated Edman degradation of the antiplatelet polypeptide and of peptides derived therefrom using an Applied Biosystems 470A gas phase sequencer equipped with a Model 900 A data system (Foster City, Calif.). Following Edman degradation, we analyzed the resulting phenylthiohydantoin (PTH) amino acids on-line using a 120 A PTH analyzer (Applied Biosystems) and a PTH-C18 column (2.1×220 mm). The PTH amino acid analyzer was calibrated prior to each sequence determination with an external standard provided by the manufacturer.

Underivatized, RCM- and RPE-antiplatelet polypeptide were all used for various sequence analyses. We determined the complete amino acid sequence of the polypeptide inhibitor of platelet activation by sequencing the amino terminal sequence of both intact and RPE-antiplatelet polypeptide, and proteolytic peptides derived from RCM-antiplatelet polypeptide. We generated the proteolytic fragments by digesting RCM-antiplatelet polypeptide with either trypsin (T-RCM-antiplatelet polypeptide) or chymotrypsin (C-RCM-antiplatelet polypeptide).

For chymotrypsin digestion, we dissolved 0.2 mg of RCM-antiplatelet polypeptide in 50 mM Tris-HCl, pH 7.5 containing 2% (w/w) of alpha-chymotrypsin (Boehringer-Mannheim, Indianapolis, Ind.) for 4 hrs at 37° C. The resulting fragments were then separated by reverse phase HPLC on a Vydac octadecylsilyl column (0.46 cm×25 cm) using a two-step gradient elution. The first step was a linear 0-28% acetonitrile gradient over 60 minutes. The second step was a 28-70% acetonitrile gradient over 5 minutes. The acetonitrile solutions all contained 0.1% TFA and both steps were performed at a flow rate of 1.0 ml/minute. The effluent stream was monitored for absorbance at 214 nm and 280 nm. We collected the peak fractions, dried them under vacuum and then subjected them to amino acid sequencing as above.

We performed trypsin digestion by dissolving 0.2 mg of RCM-antiplatelet polypeptide in 50 mM Tris, pH 7.5 containing 2% trypsin (w/w) (Boehringer-Mannheim). The resulting fragments were separated using the same C18 column as described above. We again employed a two-step gradient. The first step was a linear acetonitrile gradient from 0-28% over 80 minutes. The second step was a linear 28-100% acetonitrile gradient over 10 minutes. Peak fractions were collected and sequenced as previously described for C-RCM-antiplatelet polypeptide.

Amino terminal sequence analysis allowed determination of residues 1-30 of the polypeptide inhibitor of platelet activation. Amino terminal sequencing of RPE-antiplatelet polypeptide provided a linear sequence of residues 1-62, confirming the first 30 amino acids. One tryptic fragment of RCM-anitplatelet polypeptide provided the sequence of amino acids 53-68. Another tryptic fragment yielded the sequence of amino acids 69-72. Residues 59-72 were determined by analysis of a chymotryptic peptide of RCM-antiplatelet polypeptide.

The complete amino acid sequence determined for the polypeptide inhibitor of platelet activation is:
EAGEE CDCGS PENPC CDAAT CKLRP GAQCA EGLCC DQCKF MKEGT VCRRA RGDDV NDYCN GISAG CPRNP FH.
As depicted above, the amino acids are represented by single letter codes as follows:

| Phe: | F | Leu: | L | Ile: | I | Met: | M | Val: | V |
|---|---|---|---|---|---|---|---|---|---|
| Ser: | S | Pro: | P | Thr: | T | Ala: | A | Tyr: | Y |
| His: | H | Gln: | Q | Asn: | N | Lys: | K | Asp: | D |
| Glu: | E | Cys: | C | Trp: | W | Arg: | R | Gly: | G |

Reaction of the intact protein with Ellman's reagent [G. E. Means and R. E. Feeney, "Chemical Modification of Protein", Holden-Day, Inc., San Francisco, Calif., pp. 155-56 (1971)] suggested the absence of free or accessible thiol groups. Analysis of the amino acid sequence revealed few lipophilic amino acids. It is probable that the large number of cysteine residues (12 moles cysteine/mole antiplatelet polypeptide) may provide a lipophilic core if the protein assumes a globular structure. We believe that this antiplatelet polypeptide inhibitor of platelet activation occurs naturally as a dimer composed of two identical subunits linked by at least two disulfide bonds.

EXAMPLE 3

Inhibition Of Platelet Aggregation And Release

We prepared platelet-rich plasma from healthy human volunteers for use in various platelet assays. More specifically, blood was collected via a 21 gauge butterfly cannula, using a two-syringe technique, into 1/10 volume of 3.8% trisodium citrate. Platelet-rich plasma was prepared by room temperature centrifugation of the citrated whole blood for 15 minutes at 100×g. The platelet rich plasma contained approximately 357,000 platelets/$\mu$l. We prepared platelet-poor plasma by centrifuging the citrated whole blood for 2 minutes at 12,000×g.

Figure 4:
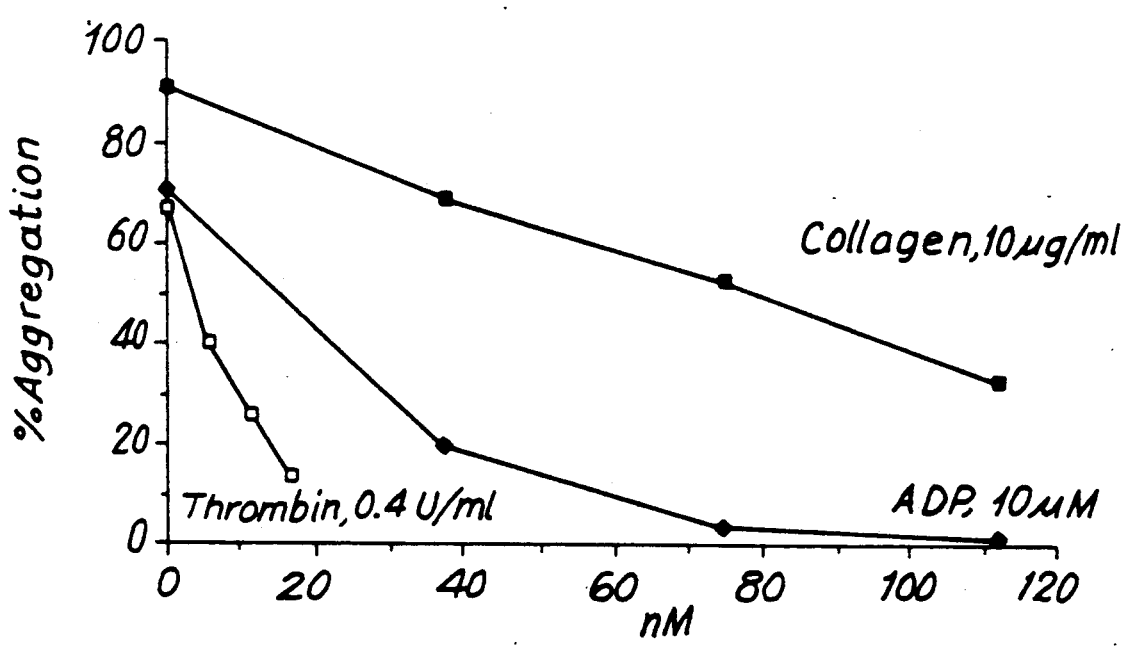
FIG. 4 depicts the inhibitory effects of varying concentrations of a polypeptide inhibitor of platelet activation of this invention on the platelet aggregating effects of collagen, thrombin and ADP.

Platelet aggregation was assayed in a 4-channel platelet aggregation profiler (PAP4, Biodata, Hatboro, Pa.) according to the manufacturer's directions. We studied inhibition of platelet aggregation effected by the antiplatelet polypeptide prepared in Example 1 by adding varying amounts of the polypeptide to stirred human platelet-rich plasma. Specifically, we incubated the polypeptide with the platelets for 1 minute at 37° C. prior to the addition of collagen (10 $\mu$g/ml), ADP (10 $\mu$M), or human $\alpha$-thrombin (0.4 U/ml). FIG. 4 demonstrates that the antiplatelet polypeptide inhibited platelet aggregation induced by collagen, ADP and thrombin in a dose-dependent manner.

Figure 5:
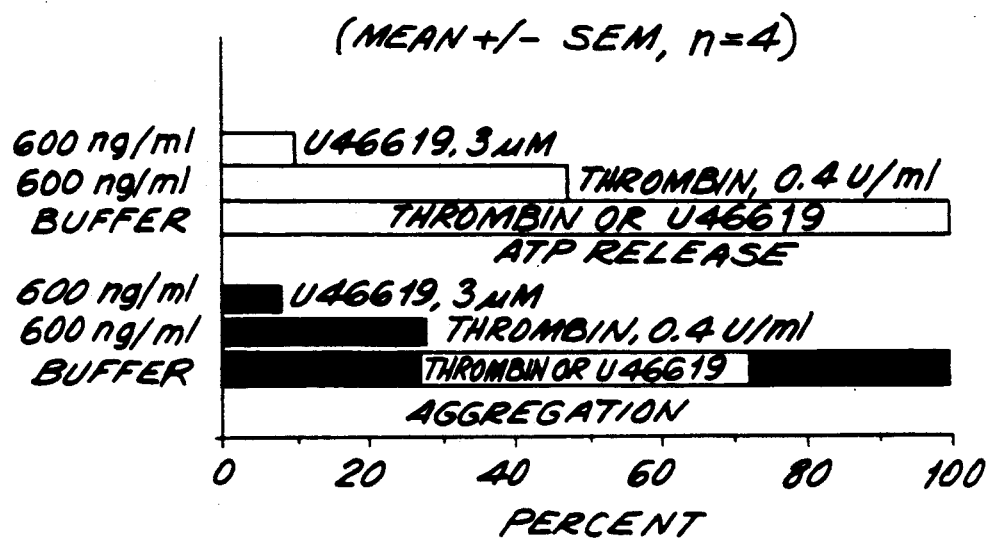
FIG. 5 depicts the inhibitory effects of a polypeptide inhibitor of platelet activation of this invention on platelet aggregation and platelet ATP secretion induced by thrombin or U46619.

We next assayed the effect of the antiplatelet polypeptide on platelet aggregation and concomitant ATP release using a Lumiaggregometer (Chronolog Corp., Havertown, Pa.). This apparatus measures aggregation turbidimetrically and, and at the same time, measures ATP release by luminescence. For this assay, we added antiplatelet polypeptide (600 ng/ml) to 0.5 ml of platelet-rich plasma at 37° C. one minute prior to the addition of human $\alpha$-thrombin (0.4 U/ml) or the thromboxane $A_2$-mimetic, U46619 (3 $\mu$M). FIG. 5 demonstrates that the polypeptide inhibitor of platelet activation effectively inhibited both platelet aggregation and ATP release induced by U46619 or thrombin, as compared to controls which were incubated without the antiplatelet polypeptide.

Figure 6:
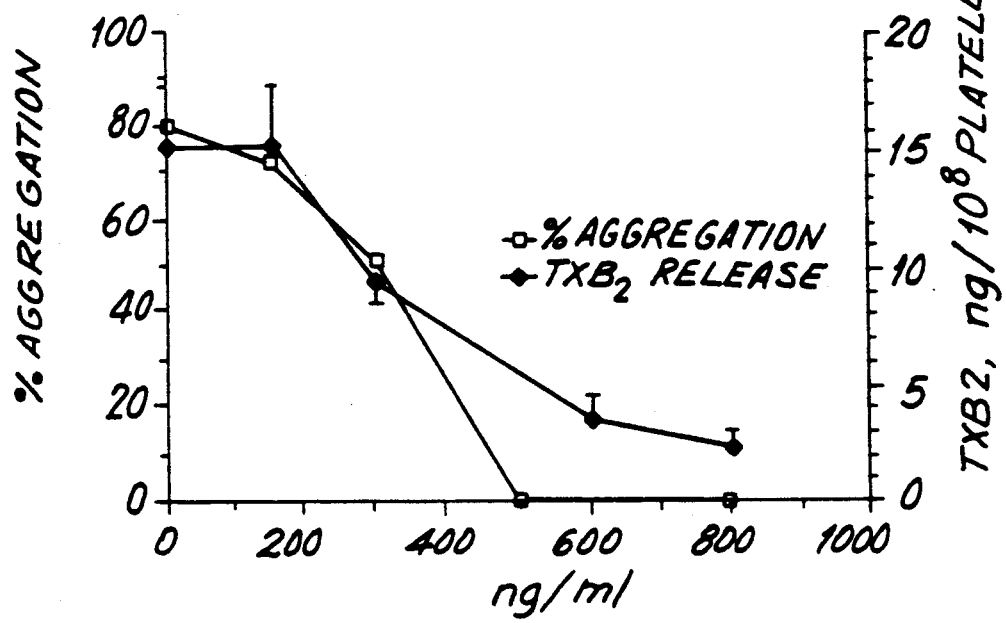
FIG. 6 depicts the inhibitory effects of varying concentrations of a polypeptide inhibitor of platelet activation of this invention on collagen-induced platelet aggregation and thromboxane $A_2$ ($TXA_2$) release.

We also assayed the ability of the antiplatelet polypeptide to inhibit collagen-stimulated platelet thromboxane $A_2$ generation and compared it to inhibition of collagen-induced platelet aggregation. In this assay, varying concentrations of antiplatelet polypeptide were added to a stirred suspension of platelet-rich plasma held at 37° C. One minute after the addition of the polypeptide, collagen was added to a final concentration of 1 $\mu$g/ml. The reaction was allowed to proceed for 4 minutes after which time it was stopped by adding ice-cold indomethacin to a final concentration of 10 $\mu$M. The suspension was then centrifuged at 12,000×g for 2 minutes and the supernatant was removed and analyzed by radioimmunoassay for released thromboxane $B_2$, a stable metabolite of thromboxane $A_2$. In the absence of any added agonist or antiplatelet polypeptide, the level of thromboxane $B_2$ detected was <0.5 ng/$10^8$ platelets. FIG. 6 demonstrates that the inhibition of platelet aggregation correlates with inhibition of thromboxane $A_2$ release.

We then analyzed the ability of the polypeptide inhibitor of platelet activation to inhibit the release of $^3$H- serotonin from platelets. Platelets, in citrated platelet-rich plasma, were loaded with [$^3$H]-serotonin or 5-hydroxy[6-$^3$H] tryptamine creatinine sulphate (Amersham, Arlington Heights, Ill.) by incubation at 37° C. for 30 minutes. Stirred [$^3$H]-serotonin loaded platelets in plasma (0.5 ml) were incubated at 37° C. with varying amounts of antiplatelet polypeptide (0–2.5 μg/ml final concentration) for 1 minute. Platelets were then stimulated by the addition of ADP (2 μM or 10 μM), human γ-thrombin (5–20 μg/ml final concentration), or collagen (10 μg/ml). Four minutes after the addition of agonist, the reaction was terminated and serotonin release and reuptake blocked by the addition of a 1/10th volume of ice-cold ETPI cocktail (3.3% EDTA, 10 mM theophylline, 1 μg/ml prostaglandin E1 and 500 μM imipramine). Following the addition of ETPI, platelets were recovered by centrifugation at 12,000×g for 2 minutes. Release was measured by liquid scintillation counting of [$^3$H]-radioactivity. The results are shown in the table below:

| Agonist | Antiplatelet polypeptide (μg/ml) | Platelet Aggregation (% of maximum) | Platelet Release (% [3H]-serotonin) |
|---|---|---|---|
| ADP (2 μM) | 0.0 | 70 | 67 |
|  | 0.5 | 32 | 0 |
|  | 1.0 | 20 | 0 |
|  | 2.0 | 9 | 0 |
|  | 5.0 | 0 | 0 |
| ADP (10 μM) | 0.0 | 57 | 29 |
|  | 0.5 | 43 | 5 |
|  | 1.0 | 41 | 2 |
|  | 2.0 | 14 | 5 |
|  | 5.0 | 0 | 0 |
| γ-thrombin (5 μg/ml) | 0.0 | 74 | 70 |
|  | 2.0 | 5 | 0 |
|  | 5.0 | 0 | 0 |
| γ-thrombin (10 μg/ml) | 0.0 | 68 | 58 |
|  | 0.5 | 63 | 34 |
|  | 2.0 | 30 | 11 |
|  | 5.0 | 0 | 6 |
| γ-thrombin (20 μg/ml) | 0.0 | 74 | 87 |
|  | 5.0 | 20 | 85 |
| collagen (10 μg/ml) | 0.0 | 72 | 74 |
|  | 0.5 | 63 | 73 |
|  | 2.0 | 50 | 60 |
|  | 3.0 | 18 | 63 |
|  | 5.0 | 0 | 23 |

Taken together, these results indicate that the effects of the antiplatelet polypeptide toward platelet aggregation and release are closely correlated and probably derive from a single mode of action. The molar IC$_{50}$ values for inhibition of platelet function by antiplatelet polypeptide are provided below:

| Agonist | Concentration | Aggregation IC$_{50}$ | Thromboxane A$_2$ IC$_{50}$ | Serotonin IC$_{50}$ |
|---|---|---|---|---|
| ADP | 2 μM | 16.5 nM | N.D. | <10 nM |
|  | 5 μM | 16.7 nM | 11.6 nM | N.D. |
|  | 10 μM | 50 nM | N.D. | 11 nM |
| γ-thrombin | 5 μg/ml | 39 nM | N.D. | <10 nM |
|  | 10 μg/ml | 64 nM | N.D. | 20 nM |
|  | 20 μg/ml | 128 nM | N.D. | N.D. |
| collagen | 1 μg/ml | 14 nM | 22 nM | N.D. |
|  | 10 μg/ml | 89 nM | N.D. | 145 nM |
| arachidonic acid | 1 mM | 11.8 nM | 13.3 nM | N.D. |

(N.D. = not determined)

The antiplatelet polypeptide was found to have an IC$_{50}$ for inhibition of platelet reactions ranging between <10 nM to 145 nM, depending on the type and concentration of agonist used. The platelet activation induced by all agonists at all concentrations used, with the exception of 10 μg/ml collagen, was completely inhibited by antiplatelet polypeptide at a concentration of 194 nM (<3.5 μg/ml).

EXAMPLE 4

Binding Of An $^{125}$I-Labelled Polypeptide Inhibitor Of Platelet Activation To Platelets We studied the binding of $^{125}$I-labeled antiplatelet polypeptide to platelets in the presence or absence of 5 μM ADP. The polypeptide was labeled with $^{125}$I-Bolton Hunter reagent as follows. We dissolved 10 μg of the polypeptide inhibitor of platelet activation, as purified in Example 1, in 25 μl of sodium borate, pH 9.0 and then added 1 mCi of $^{125}$I-Bolton-Hunter reagent (New England Nuclear, Boston, Mass.). The reaction was allowed to proceed for 30 minutes at room temperature. The iodination was stopped by the addition of a 1000-fold molar excess of glycine. $^{125}$I-antiplatelet polypeptide was removed from free $^{125}$I-Bolton-Hunter reagent by desalting on a column of Sephadex G-25 equilibrated in phosphate buffered saline. $^{125}$I-antiplatelet polypeptide (15.2×10$^6$ cpm/μg) was diluted with unlabeled antiplatelet polypeptide to a concentration of 200 μg/ml.

Figure 7:
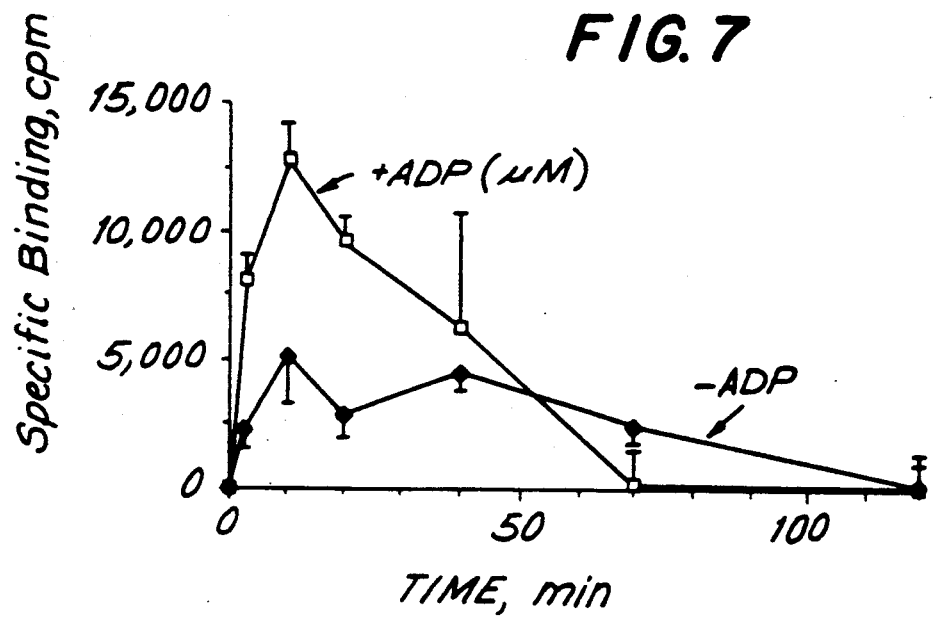
FIG. 7 depicts the kinetics of binding of a $^{125}$I-labeled polypeptide inhibitor of platelet activation of this invention to platelets in the presence or absence of ADP.

Binding of $^{125}$I-antiplatelet polypeptide was performed by incubating 1.0 ml of human platelet rich plasma in the presence or absence of ADP (5 μM) for 1 minute prior to the addition of radiolabeled antiplatelet polypeptide (2 ng/ml final concentration) or radiolabeled antiplatelet polypeptide plus 100-fold molar excess of unlabeled antiplatelet polypeptide. The kinetics of specific $^{125}$I-antiplatelet polypeptide binding was measured by removing 0.1 ml aliquots of the platelet suspension at various time intervals (0–120 minutes). The aliquots were applied to the top of 0.1 ml of 30% sucrose and centrifuged at 12,000× g for 3 minutes An aliquot of the supernatant (50 μl ) was counted for radioactivity in a gamma counter instrument. FIG. 7 shows that the binding of antiplatelet polypeptide to both ADP-stimulated and unstimulated platelets is maximal after 10 minutes. This figure also shows that the antiplatelet polypeptide binds ADP-stimulated platelets with a 2.5-fold higher affinity than unstimulated platelets.

EXAMPLE 5

Combined Effects Of The Polypeptide Inhibitor of Platelet Activation And A Synthetic Antithrombin Agent To determine the effectiveness of combinations of the polypeptide inhibitor of platelet activation together with other anti-thrombin agents in inhibiting platelet aggregation, we performed a thrombin-induced platelet aggregation assay. Specifically, we incubated 0.5 ml of stirred plateletrich plasma with varying concentrations of antiplatelet polypeptide, as purified in Example 1, (0–160 ng/ml), Sulfo-Tyr$_{63}$hirudin$_{53-64}$ (0–115 ng/ml) or a combination of the two inhibitors.

The Asn-Gly-Asp-Phe-Glu-Glu-Ile-Pro-Glu-Glu-Tyr-Leu amino acid backbone of Sulfo-Tyr$_{63}$hirudin$_{53-64}$ was synthesized by solid phase peptide synthesis techniques employing an Applied Biosystems 430 A Peptide Synthesizer (Applied Biosystems, Foster City, Calif.). The peptide was then sulfated at the single tyrosine residue by dissolving 1 gram of peptide in 40 ml of dimethyl formamide in the presence of 5 ml of N,N'-dicyclohexylcarbodiimide (0.2 g/0.16 ml dimethylformamide). The mixture was stirred at 0° C. and 0.5 ml of concentrated sulfuric acid was added dropwise to the reaction mixture until precipitate formed. The reaction was stopped by the addition of 40 ml of water and purification of Sulfo-Tyr$_{63}$hirudin$_{53-64}$ was achieved by DEAE-Sepharose chromatography. The column was developed with a 0–0.4M linear gradient of NaCl. The desired product eluted at 0.2–0.3M NaCl.

Figure 8:
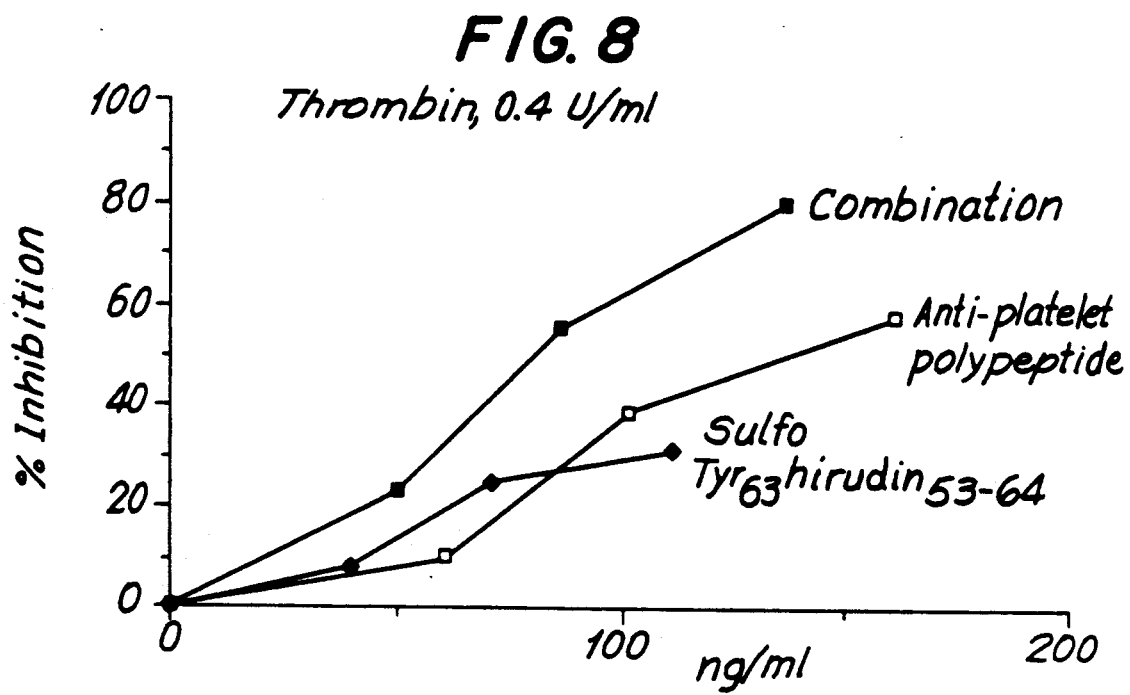
FIG. 8 depicts the inhibitory effects of a polypeptide inhibitor of platelet activation of this invention, the anti-thrombin polypeptide Sulfo-Tyr$_{63}$hirudin$_{53-64}$ and combinations thereof on thrombin-induced platelet aggregation.

After 1 minute, human α-thrombin was added to the sample to a final concentration of 0.4 U/ml. Platelet aggregation was measured in the PAP4 apparatus, as previously described herein. FIG. 8 demonstrates that the antiplatelet polypeptide and Sulfo-Tyr$_{63}$hirudin$_{53-64}$ have an additive effect of inhibiting thrombin-induced platelet aggregation when utilized together.

EXAMPLE 6

Preparation Of A Recombinant Polypeptide Inhibitor Of Platelet Activation

Figure 12:
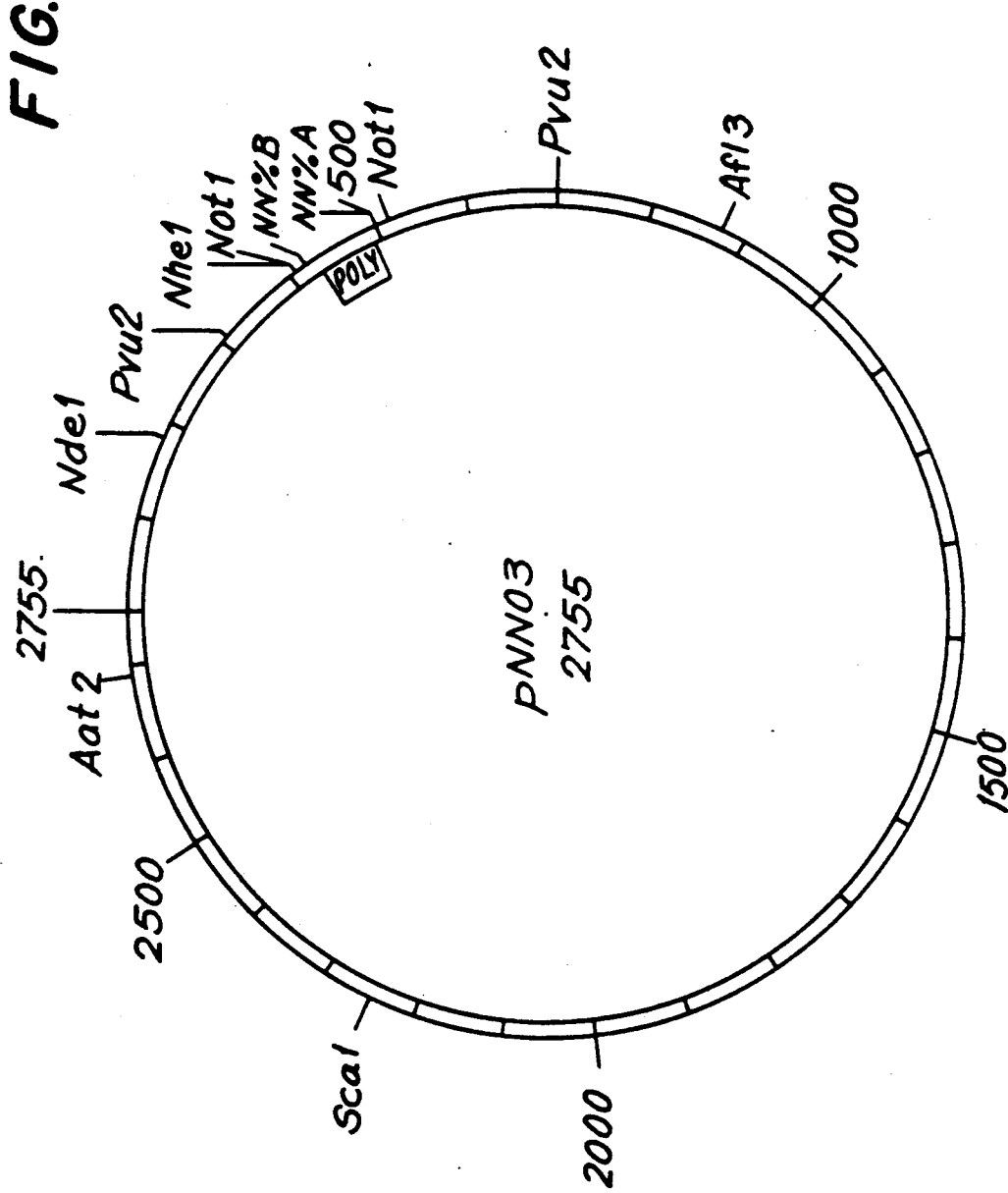
FIG. 12 depicts the restriction endonuclease map of pNN03.

A synthetic gene encoding an antiplatelet polypeptide of this invention (FIG. 9) was designed using the complete amino acid sequence of the natural protein and a back-translation computer program (University of Wisconsin, Genetic Computer Group, Sequence Analysis Software Package, Version 5.2). The total gene, 229 base pairs, is synthesized as 14 different oligomers which, when ligated together, form the restriction sequences shown in FIG. 9. As illustrated in FIG. 10, the 14 oligomers are synthesized as 7 essentially complementary pairs of oligonucleotides. The protruding sequences at joining sites of complementary pairs of oligomers are 6 bases in length. The 14 oligomers are assembled in the cloning vector pNN03. Plasmid pNN03 is a derivative of the commercially available plasmid pUC8. It is created by cleaving out the entire polylinker region of pUC8 by digestion with HindIII and EcoRI. An alternate polylinker containing different restriction sites (FIG. 11) is synthesized by standard procedures and ligated in the HindIII/EcoRI-cleaved pUC8. A restriction map of pNN03 is depicted in FIG. 12.

Plasmid pNN03 is cleaved with restriction enzymes NcoI and HindIII. The 14 oligomers are added to the cleaved vector and ligation is achieved with T4 ligase. E.coli cells are then transfected with the ligated mixture and colonies expressing tetracycline resistance are isolated. Plasmids are isolated from these colonies and examined by restriction mapping and nucleotide sequencing to determine if they contain the intact synthetic antiplatelet polypeptide gene. After demonstrating the integrity of an assembled vector, the isolated plasmid is cleaved with NcoI and HindIII to release the gene encoding the antiplatelet polypeptide. The gene is then ligated into the expression vector P$_L$-mu-smc$^{tetR}$, which has been cleaved with the same two restriction enzymes. P$_L$-mu-smc$^{tetR}$ is tetracycline resistant derivative of P$_L$-mu-smc$^{ampR}$ previously described in PCT patent application WO 86/05810. The complete nucleotide sequence of P$_L$-mu-smc$^{tetR}$ is depicted in FIG. 13. The ligated vector is used to transfect E.coli and expression of recombinant antiplatelet polypeptide is achieved by temperature induction of the P$_L$ promoter.

While we have hereinbefore described a number of embodiments of this invention, it is apparent that our basic constructions can be altered to provide other embodiments which utilize the polypeptides, pharmaceutical compositions and combinations and recombinant DNA molecules of this invention. Therefore, it will be appreciated that the scope of this invention is to be defined by the claims appended hereto rather than by specific embodiments which have been presented hereinbefore by way of example.

We claim:

1. A snake venom polypeptide inhibitor of platelet activation substantially free of other snake venom components, wherein said polypeptide consists essentially of two homologous disulfide-linked polypeptide chains, each of said polypeptide chains having the amino acid formula: EAGEE CDCGS PENPC CDAAT CKLRP GAQCA EGLCC DQCKF MKEGT VCRRA RGDDV NDYCN GISAG CPRNP FH.

2. A recombinant DMA molecule which comprises a DNA sequence coding on expression for a polypeptide inhibitor of platelet activation according to claim 1, said DNA sequence being selected from the group consisting of:
   (a) ATG GAA GCT GGT GAA GAA TGC GAC TGC GGA TCC CCG GAA AAC CCG TGC TGC GAC GCG GCC ACC TGC AAA CTT CGT CCG GGT GCA CAG TGT GCA GAA GGT CTG TGC TGC GAC CAG TGC AAA TTC ATG AAA GAA GGT ACC GTT TGC CGT CGT GCT CGA GGT GAC GAC GTT AAC GAC TAC TGC AAC GGT ATC TCT GCA GGT TGC CCG CGT AAC CCG TTC CAC;
   (b) DNA sequences which hybridize to the DNA sequence of (a) and which code on expression for a polypeptide inhibitor of platelet activation according to claim 1; and
   (c) DNA sequences other than the DNA sequences of (a) or (b) which code on expression for a polypeptide inhibitor of platelet-activation according to claim 1.

3. A host transformed with the recombinant DNA molecule according to claim 2, said host being selected from the group consisting of animal cells, plant cells, insect cells, yeast and other fungi and bacteria.

4. A process for producing a polypeptide inhibitor of platelet activation comprising the step of culturing a host according to claim 3.

5. A polypeptide inhibitor of platelet activation produced by the process according to claim 4.

6. A pharmaceutically acceptable composition for decreasing or inhibiting platelet aggregation and platelet release in a patient or extracorporeal blood comprising a pharmaceutically acceptable carrier and a polypeptide according to claim 1.

7. The composition according to claim 6, wherein the amount of said polypeptide is between about 0.64 and 6,400 mg.

8. The composition according to claim 6, wherein the amount of said polypeptide is between about 0.215 and 43 mg.

9. A composition for coating the surface of an invasive device to be inserted into a patient comprising a polypeptide according to claim 1 and a component suitable for coating said invasive device with said polypeptide.

* * * * *